(12) United States Patent
Nguyen et al.

(10) Patent No.: US 7,896,892 B2
(45) Date of Patent: *Mar. 1, 2011

(54) MULTIPLE BIAS SURGICAL FASTENER

(75) Inventors: John Nguyen, San Jose, CA (US); Nga T. Doan, San Jose, CA (US); Laurent Schaller, Los Altos, CA (US)

(73) Assignee: Medtronic, Inc., Minneapolis, MN (US)

( * ) Notice: Subject to any disclaimer, the term of this patent is extended or adjusted under 35 U.S.C. 154(b) by 776 days.

This patent is subject to a terminal disclaimer.

(21) Appl. No.: 10/408,019

(22) Filed: Apr. 3, 2003

(65) Prior Publication Data

US 2003/0191481 A1    Oct. 9, 2003

Related U.S. Application Data

(63) Continuation of application No. 09/541,397, filed on Mar. 31, 2000, now Pat. No. 6,551,332.

(51) Int. Cl.
*A61B 17/08* (2006.01)

(52) U.S. Cl. .......................... 606/151; 606/153; 606/213

(58) Field of Classification Search .................. 606/151, 606/153, 157, 158, 191, 219–221, 200, 78; 29/34 D, 896.8, 402.21; 24/67.3, 67.5; 128/830, 128/831; 267/166, 168, 177; 623/1.18
See application file for complete search history.

(56) References Cited

U.S. PATENT DOCUMENTS

| | | | |
|---|---|---|---|
| 43,098 A | 6/1864 | Cooper | |
| 636,728 A | 11/1899 | Kindel | |
| 655,190 A | 8/1900 | Bramson | |
| 1,087,186 A | * 2/1914 | Scholfield | ..................... 267/166 |
| 1,167,014 A | 1/1916 | O'Brien | |
| 1,539,221 A | 5/1925 | John | |
| 1,583,271 A | 5/1926 | Biro | |
| 1,625,602 A | 4/1927 | Gould et al. | |
| 1,867,624 A | 7/1932 | Hoffman | |
| 2,201,610 A | 5/1940 | Dawson | |
| 2,240,330 A | 4/1941 | Flagg et al. | |
| 2,256,382 A | 9/1941 | Dole | |
| 2,264,679 A | 12/1941 | Ravel | |
| 2,413,142 A | 12/1946 | Jones et al. | |

(Continued)

FOREIGN PATENT DOCUMENTS

DE    21 99 99    3/1910

(Continued)

OTHER PUBLICATIONS

Chitwood Jr., Mitral Valve Repair: Ischemic, Mastery of Cardiothoracic Surgery, Lippencott-Raven Publishers, 1998, Chapter 32, pp. 309-321.

(Continued)

*Primary Examiner* — Julian W Woo
(74) *Attorney, Agent, or Firm* — Mark Jaro; Katrina A. Witschen

(57) ABSTRACT

A surgical fastener comprising a clip movable between an open configuration and a closed configuration and a biasing member contacting the clip and biasing the clip to its open configuration when the biasing member is actuated. The biasing member and clip both tend to assume the closed configuration when no external forces are applied to them. A needle may be releasably attached to the clip. Methods for making the fasteners are also disclosed, in which both the clip and the biasing member are set in the closed position.

17 Claims, 21 Drawing Sheets

U.S. PATENT DOCUMENTS

| | | |
|---|---|---|
| 2,430,293 A | 11/1947 | Howells |
| 2,505,358 A | 4/1950 | Gusberg et al. |
| 2,516,710 A | 7/1950 | Mascolo |
| 2,715,486 A | 8/1955 | Marcoff-Moghadam et al. |
| 2,890,519 A | 6/1959 | Storz, Jr. |
| 2,940,452 A | 6/1960 | Smialowski |
| 3,055,689 A * | 9/1962 | Jorgensen .................. 267/177 |
| 3,057,355 A | 10/1962 | Smialowski |
| 3,082,426 A | 3/1963 | Miles |
| 3,143,742 A | 8/1964 | Cromie |
| 3,150,379 A | 9/1964 | Brown |
| 3,180,337 A | 4/1965 | Smialowski |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| 3,656,185 A | 4/1972 | Carpentier |
| RE27,391 E | 6/1972 | Merser |
| 3,753,438 A | 8/1973 | Wood et al. |
| 3,762,418 A | 10/1973 | Wasson |
| 3,776,237 A | 12/1973 | Hill et al. |
| 3,802,438 A | 4/1974 | Wolvek |
| 3,825,009 A | 7/1974 | Williams |
| 3,837,345 A | 9/1974 | Matar |
| 3,874,388 A | 4/1975 | King et al. |
| 3,875,648 A | 4/1975 | Bone |
| 3,905,403 A * | 9/1975 | Smith et al. .................. 267/168 |
| 3,908,662 A | 9/1975 | Razqulov et al. |
| 3,910,281 A | 10/1975 | Kletschka et al. |
| 3,958,576 A | 5/1976 | Komiya |
| 3,976,079 A | 8/1976 | Samuels |
| 3,995,619 A | 12/1976 | Glatzer |
| 4,006,747 A | 2/1977 | Kronenthal et al. |
| 4,018,228 A | 4/1977 | Goosen |
| 4,038,725 A | 8/1977 | Keefe |
| 4,042,979 A | 8/1977 | Angell |
| 4,073,179 A | 2/1978 | Hickey et al. |
| 4,103,690 A | 8/1978 | Harris |
| 4,111,206 A | 9/1978 | Vishnevsky et al. |
| 4,129,059 A | 12/1978 | Van Eck |
| 4,140,125 A | 2/1979 | Smith |
| 4,170,990 A | 10/1979 | Baumgart et al. |
| 4,185,636 A | 1/1980 | Gabbay et al. |
| 4,192,315 A | 3/1980 | Hilzinger et al. |
| 4,214,587 A | 7/1980 | Sakura |
| 4,217,902 A | 8/1980 | March |
| 4,243,048 A | 1/1981 | Griffin |
| 4,324,248 A | 4/1982 | Perlin |
| 4,345,601 A | 8/1982 | Fukuda |
| 4,352,358 A | 10/1982 | Angelchik |
| 4,366,819 A | 1/1983 | Kaster |
| 4,396,139 A | 8/1983 | Hall et al. |
| 4,416,266 A | 11/1983 | Baucom |
| 4,456,017 A | 6/1984 | Miles |
| 4,465,071 A | 8/1984 | Samuels et al. |
| 4,470,415 A | 9/1984 | Wozniak |
| 4,470,533 A | 9/1984 | Schuler |
| 4,474,181 A | 10/1984 | Schenck |
| 4,485,816 A | 12/1984 | Krumme |
| 4,492,229 A | 1/1985 | Grunwald |
| 4,522,207 A | 6/1985 | Klieman et al. |
| 4,523,592 A | 6/1985 | Daniel |
| 4,532,927 A | 8/1985 | Miksza |
| 4,535,764 A | 8/1985 | Ebert |
| 4,549,545 A | 10/1985 | Levy |
| 4,553,542 A | 11/1985 | Schenck et al. |
| 4,576,605 A | 3/1986 | Kaidash et al. |
| 4,586,502 A | 5/1986 | Bedi et al. |
| 4,586,503 A | 5/1986 | Kirsch et al. |
| 4,593,693 A | 6/1986 | Schenck |
| 4,595,007 A | 6/1986 | Mericle |
| 4,612,932 A | 9/1986 | Caspar et al. |
| 4,622,970 A | 11/1986 | Wozniak |
| 4,624,255 A | 11/1986 | Schenck et al. |
| 4,637,380 A | 1/1987 | Orejola |
| 4,641,652 A | 2/1987 | Hutterer et al. |
| 4,653,496 A | 3/1987 | Bundy et al. |
| 4,665,906 A | 5/1987 | Jervis |
| 4,665,917 A | 5/1987 | Clanton et al. |
| 4,683,895 A | 8/1987 | Pohndorf |
| 4,706,362 A | 11/1987 | Strausburg |
| 4,719,917 A | 1/1988 | Barrows et al. |
| 4,719,924 A | 1/1988 | Crittenden et al. |
| 4,730,615 A | 3/1988 | Sutherland et al. |
| 4,732,151 A | 3/1988 | Jones |
| 4,809,695 A | 3/1989 | Gwathmey et al. |
| 4,820,298 A * | 4/1989 | Leveen et al. ................. 623/1.18 |
| 4,844,318 A | 7/1989 | Kunreuther |
| 4,873,975 A | 10/1989 | Walsh et al. |
| 4,890,615 A | 1/1990 | Caspari et al. |
| 4,896,668 A | 1/1990 | Popoff et al. |
| 4,899,744 A | 2/1990 | Fujitsuka et al. |
| 4,901,721 A | 2/1990 | Hakki |
| 4,923,461 A | 5/1990 | Caspari et al. |
| 4,924,866 A | 5/1990 | Yoon |
| 4,926,860 A | 5/1990 | Stice et al. |
| 4,929,240 A | 5/1990 | Kirsch et al. |
| 4,930,674 A | 6/1990 | Barak |
| 4,932,955 A | 6/1990 | Merz et al. |
| 4,935,027 A | 6/1990 | Yoon |
| 4,950,015 A | 8/1990 | Nejib et al. |
| 4,950,283 A | 8/1990 | Dzubow et al. |
| 4,950,285 A | 8/1990 | Wilk |
| 4,957,498 A | 9/1990 | Caspari et al. |
| 4,983,176 A | 1/1991 | Cushman et al. |
| 4,990,152 A | 2/1991 | Yoon |
| 4,991,567 A | 2/1991 | McCuen et al. |
| 4,994,069 A | 2/1991 | Ritchart et al. |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,007,920 A | 4/1991 | Torre |
| 5,011,481 A | 4/1991 | Myers et al. |
| 5,020,713 A | 6/1991 | Kunreuther |
| 5,026,379 A | 6/1991 | Yoon |
| 5,032,127 A | 7/1991 | Frazee et al. |
| 5,035,692 A | 7/1991 | Lyon et al. |
| 5,035,702 A | 7/1991 | Taheri |
| 5,042,707 A | 8/1991 | Taheri |
| 5,047,047 A | 9/1991 | Yoon |
| 5,053,047 A | 10/1991 | Yoon |
| 5,064,431 A | 11/1991 | Gilbertson et al. |
| 5,074,874 A | 12/1991 | Yoon et al. |
| 5,088,692 A | 2/1992 | Weiler |
| 5,100,418 A | 3/1992 | Yoon |
| 5,100,421 A | 3/1992 | Christoudias |
| 5,104,407 A | 4/1992 | Lam et al. |
| 5,119,983 A | 6/1992 | Green et al. |
| 5,123,913 A | 6/1992 | Wilk et al. |
| 5,127,413 A | 7/1992 | Ebert |
| 5,129,913 A | 7/1992 | Ruppert |
| 5,152,769 A | 10/1992 | Baber |
| 5,154,189 A | 10/1992 | Oberlander |
| 5,158,566 A | 10/1992 | Pianetti |
| 5,171,250 A | 12/1992 | Yoon |
| 5,171,252 A | 12/1992 | Friedland |
| 5,174,087 A | 12/1992 | Bruno |

| | | | | | | |
|---|---|---|---|---|---|---|
| 5,178,634 A | 1/1993 | Ramos Martinez | | 5,496,334 A | 3/1996 | Klundt et al. |
| 5,192,294 A | 3/1993 | Blake | | 5,499,990 A | 3/1996 | Schulken et al. |
| 5,196,022 A | 3/1993 | Bilweis | | 5,500,000 A | 3/1996 | Feagin et al. |
| 5,201,880 A | 4/1993 | Wright et al. | | 5,522,884 A | 6/1996 | Wright |
| 5,207,694 A | 5/1993 | Broome | | 5,527,342 A | 6/1996 | Pietrzak et al. |
| 5,217,027 A | 6/1993 | Hermens | | 5,533,236 A | 7/1996 | Tseng |
| 5,219,358 A | 6/1993 | Bendel et al. | | 5,538,509 A | 7/1996 | Dunlap et al. |
| 5,221,259 A | 6/1993 | Weldon et al. | | 5,545,214 A | 8/1996 | Stevens |
| 5,222,961 A | 6/1993 | Nakao et al. | | 5,549,619 A | 8/1996 | Peters et al. |
| 5,222,976 A | 6/1993 | Yoon | | 5,556,411 A | 9/1996 | Taoda et al. |
| 5,234,447 A | 8/1993 | Kaster et al. | | 5,562,685 A | 10/1996 | Mollenauer et al. |
| 5,236,440 A | 8/1993 | Hlavacek | | 5,569,205 A | 10/1996 | Hart et al. |
| 5,242,456 A | 9/1993 | Nash et al. | | 5,569,274 A | 10/1996 | Rapacki et al. |
| 5,242,457 A | 9/1993 | Akopov et al. | | 5,569,301 A | 10/1996 | Granger et al. |
| 5,246,443 A | 9/1993 | Mai | | 5,571,119 A | 11/1996 | Atala |
| 5,250,053 A | 10/1993 | Snyder | | 5,571,175 A | 11/1996 | Vanney et al. |
| 5,258,011 A | 11/1993 | Drews | | 5,582,616 A | 12/1996 | Bolduc et al. |
| 5,261,917 A | 11/1993 | Hasson et al. | | 5,582,619 A * | 12/1996 | Ken ........................... 606/191 |
| 5,269,783 A | 12/1993 | Sander | | 5,584,879 A | 12/1996 | Reimold et al. |
| 5,269,809 A | 12/1993 | Hayhurst et al. | | 5,586,983 A | 12/1996 | Sanders et al. |
| 5,282,825 A | 2/1994 | Muck et al. | | 5,591,179 A | 1/1997 | Edelstein |
| 5,290,289 A | 3/1994 | Sanders et al. | | 5,593,414 A | 1/1997 | Shipp et al. |
| 5,304,117 A | 4/1994 | Wilk | | 5,593,424 A | 1/1997 | Northrup III |
| 5,304,204 A | 4/1994 | Bregen | | 5,597,378 A | 1/1997 | Jervis |
| 5,306,296 A | 4/1994 | Wright et al. | | 5,601,571 A | 2/1997 | Moss |
| 5,312,436 A | 5/1994 | Coffey et al. | | 5,601,572 A | 2/1997 | Middleman et al. |
| 5,314,468 A | 5/1994 | Ramos Martinez | | 5,601,600 A | 2/1997 | Ton |
| 5,330,503 A | 7/1994 | Yoon | | 5,603,718 A | 2/1997 | Xu |
| 5,334,196 A | 8/1994 | Scott et al. | | 5,609,608 A | 3/1997 | Benett et al. |
| 5,336,233 A | 8/1994 | Chen | | 5,618,311 A | 4/1997 | Gryskiewicz et al. |
| 5,336,239 A | 8/1994 | Gimpelson | | 5,628,757 A | 5/1997 | Hasson |
| 5,346,459 A | 9/1994 | Allen | | 5,630,540 A | 5/1997 | Blewett |
| 5,350,420 A | 9/1994 | Cosgrove et al. | | 5,632,752 A | 5/1997 | Buelna |
| 5,353,804 A | 10/1994 | Kornberg et al. | | 5,632,753 A | 5/1997 | Loeser |
| 5,355,897 A | 10/1994 | Pietrafitta et al. | | 5,643,295 A | 7/1997 | Yoon |
| 5,356,424 A | 10/1994 | Buzerak et al. | | 5,643,305 A | 7/1997 | Al-Tameem |
| 5,364,406 A | 11/1994 | Sewell | | 5,645,568 A | 7/1997 | Chervitz et al. |
| 5,366,459 A | 11/1994 | Yoon | | 5,653,716 A | 8/1997 | Malo et al. |
| 5,366,462 A | 11/1994 | Kaster et al. | | 5,653,718 A | 8/1997 | Yoon |
| 5,366,479 A | 11/1994 | McGarry et al. | | 5,658,312 A | 8/1997 | Green et al. |
| 5,374,268 A | 12/1994 | Sander | | 5,660,186 A | 8/1997 | Bachir |
| 5,376,096 A | 12/1994 | Foster | | 5,665,109 A | 9/1997 | Yoon |
| 5,376,101 A | 12/1994 | Green et al. | | 5,669,918 A | 9/1997 | Balazs et al. |
| 5,382,259 A * | 1/1995 | Phelps et al. .................. 606/151 | | 5,676,670 A | 10/1997 | Kim |
| 5,383,904 A | 1/1995 | Totakura et al. | | 5,683,417 A | 11/1997 | Cooper |
| 5,387,227 A | 2/1995 | Grice | | 5,690,662 A | 11/1997 | Chiu et al. |
| 5,403,331 A | 4/1995 | Chesterfield | | 5,695,504 A | 12/1997 | Gifford, III et al. |
| 5,403,333 A | 4/1995 | Kaster et al. | | 5,695,505 A | 12/1997 | Yoon |
| 5,403,338 A | 4/1995 | Milo | | 5,697,913 A | 12/1997 | Sierocuk et al. |
| 5,403,346 A | 4/1995 | Loeser | | 5,697,943 A | 12/1997 | Sauer et al. |
| 5,413,584 A | 5/1995 | Schulze | | 5,700,270 A | 12/1997 | Peyser et al. |
| 5,417,684 A | 5/1995 | Jackson et al. | | 5,700,271 A | 12/1997 | Whitfield et al. |
| 5,417,700 A | 5/1995 | Egan | | 5,702,412 A | 12/1997 | Popov et al. |
| 5,423,821 A | 6/1995 | Pasque | | 5,707,362 A | 1/1998 | Yoon |
| 5,431,666 A | 7/1995 | Sauer et al. | | 5,707,380 A | 1/1998 | Hinchliffe et al. |
| 5,437,680 A | 8/1995 | Yoon | | 5,709,693 A | 1/1998 | Taylor |
| 5,437,681 A | 8/1995 | Meade et al. | | 5,709,695 A | 1/1998 | Northrup, III |
| 5,437,685 A | 8/1995 | Blasnik | | 5,715,987 A | 2/1998 | Kelley et al. |
| 5,439,479 A | 8/1995 | Shichman et al. | | 5,716,370 A | 2/1998 | Williamson, IV et al. |
| 5,445,167 A | 8/1995 | Yoon et al. | | 5,720,755 A | 2/1998 | Dakov |
| 5,445,644 A | 8/1995 | Pietrafitta et al. | | 5,725,539 A | 3/1998 | Matern |
| 5,450,860 A | 9/1995 | O'Connor | | 5,725,542 A | 3/1998 | Yoon |
| 5,451,231 A | 9/1995 | Rabenau et al. | | 5,725,554 A | 3/1998 | Simon et al. |
| 5,452,733 A | 9/1995 | Sterman et al. | | 5,728,135 A | 3/1998 | Bregen et al. |
| 5,454,834 A | 10/1995 | Boebel et al. | | 5,732,872 A | 3/1998 | Bolduc et al. |
| 5,456,246 A | 10/1995 | Schmieding et al. | | 5,735,290 A | 4/1998 | Sterman et al. |
| 5,462,561 A | 10/1995 | Voda | | 5,746,753 A | 5/1998 | Sullivan et al. |
| 5,474,557 A | 12/1995 | Mai | | 5,755,778 A | 5/1998 | Kleshinski |
| 5,480,405 A | 1/1996 | Yoon | | 5,766,189 A | 6/1998 | Matsumo |
| 5,486,187 A | 1/1996 | Schenck | | 5,769,870 A | 6/1998 | Salahich et al. |
| 5,486,197 A | 1/1996 | Le et al. | | 5,779,718 A | 7/1998 | Green et al. |
| 5,488,958 A | 2/1996 | Topel et al. | | 5,782,397 A | 7/1998 | Koukline |

| | | | | | | |
|---|---|---|---|---|---|---|
| 5,782,844 | A | 7/1998 | Yoon et al. | 6,007,544 A | 12/1999 | Kim |
| 5,797,920 | A | 8/1998 | Kim | 6,010,531 A | 1/2000 | Donlon et al. |
| 5,797,933 | A | 8/1998 | Snow et al. | 6,013,084 A | 1/2000 | Ken et al. |
| 5,797,934 | A | 8/1998 | Rygaard | 6,022,367 A | 2/2000 | Sherts |
| 5,797,960 | A | 8/1998 | Stevens et al. | 6,024,748 A | 2/2000 | Manzo et al. |
| 5,799,661 | A | 9/1998 | Boyd et al. | 6,032,849 A | 3/2000 | Mastri et al. |
| 5,799,857 | A | 9/1998 | Robertson et al. | 6,033,419 A | 3/2000 | Hamblin, Jr. et al. |
| 5,810,848 | A | 9/1998 | Hayhurst | 6,036,699 A | 3/2000 | Andreas et al. |
| 5,810,851 | A | 9/1998 | Yoon | 6,036,703 A | 3/2000 | Evans et al. |
| 5,810,853 | A | 9/1998 | Yoon | 6,036,710 A | 3/2000 | McGarry et al. |
| 5,810,882 | A | 9/1998 | Bolduc et al. | 6,042,607 A | 3/2000 | Williamson et al. |
| 5,817,113 | A | 10/1998 | Gifford, III et al. | 6,056,751 A | 5/2000 | Fenton |
| 5,820,631 | A | 10/1998 | Nobles | 6,063,070 A | 5/2000 | Eder |
| 5,824,002 | A | 10/1998 | Gentelia et al. | 6,066,148 A | 5/2000 | Rygaard |
| 5,824,008 | A | 10/1998 | Bolduc et al. | 6,074,401 A | 6/2000 | Gardiner et al. |
| 5,827,265 | A | 10/1998 | Glinsky et al. | 6,074,418 A | 6/2000 | Buchanan et al. |
| 5,827,316 | A | 10/1998 | Young et al. | 6,077,291 A | 6/2000 | Das |
| 5,830,221 | A | 11/1998 | Stein et al. | 6,080,114 A | 6/2000 | Russin |
| 5,830,222 | A | 11/1998 | Makower | 6,083,237 A | 7/2000 | Huitema et al. |
| 5,833,698 | A | 11/1998 | Hinchliffe | 6,106,538 A | 8/2000 | Shiber |
| 5,849,019 | A | 12/1998 | Yoon | 6,110,188 A | 8/2000 | Narciso |
| 5,851,216 | A | 12/1998 | Allen | 6,113,611 A | 9/2000 | Allen et al. |
| 5,855,614 | A | 1/1999 | Stevens et al. | 6,113,612 A | 9/2000 | Swanson et al. |
| 5,868,702 | A | 2/1999 | Stevens et al. | 6,120,524 A | 9/2000 | Taheri |
| 5,868,763 | A | 2/1999 | Spence et al. | 6,132,438 A | 10/2000 | Fleischmann et al. |
| 5,871,528 | A | 2/1999 | Camps et al. | 6,139,540 A | 10/2000 | Rost et al. |
| 5,879,371 | A | 3/1999 | Gardiner et al. | 6,143,004 A | 11/2000 | Davis et al. |
| 5,881,943 | A | 3/1999 | Heck et al. | 6,149,658 A | 11/2000 | Gardiner et al. |
| 5,882,340 | A | 3/1999 | Yoon | 6,152,935 A | 11/2000 | Kammerer et al. |
| 5,891,130 | A | 4/1999 | Palermo et al. | 6,152,937 A | 11/2000 | Peterson et al. |
| 5,891,160 | A | 4/1999 | Williamson, IV et al. | 6,159,165 A | 12/2000 | Ferrera et al. |
| 5,893,369 | A | 4/1999 | LeMole | 6,159,225 A | 12/2000 | Makower |
| 5,893,865 | A | 4/1999 | Swindle et al. | 6,162,233 A | 12/2000 | Williamson, IV et al. |
| 5,893,886 | A | 4/1999 | Zegdi et al. | 6,165,183 A | 12/2000 | Kuehn et al. |
| 5,895,394 | A | 4/1999 | Kienzle et al. | 6,165,185 A | 12/2000 | Shennib et al. |
| 5,904,697 | A | 5/1999 | Gifford, III et al. | 6,171,320 B1 | 1/2001 | Monassevitch |
| 5,908,428 | A | 6/1999 | Scirica et al. | 6,171,321 B1 | 1/2001 | Gifford, III et al. |
| 5,911,352 | A | 6/1999 | Racenet et al. | 6,176,413 B1 | 1/2001 | Heck et al. |
| 5,919,207 | A | 7/1999 | Taheri | 6,176,864 B1 | 1/2001 | Chapman |
| 5,931,842 | A | 8/1999 | Goldsteen et al. | 6,179,840 B1 | 1/2001 | Bowman |
| 5,941,434 | A | 8/1999 | Green | 6,179,848 B1 | 1/2001 | Solem |
| 5,941,442 | A | 8/1999 | Geiste et al. | 6,179,849 B1 | 1/2001 | Yencho et al. |
| 5,941,888 | A | 8/1999 | Wallace et al. | 6,183,512 B1 | 2/2001 | Howanec et al. |
| 5,941,908 | A | 8/1999 | Goldsteen et al. | 6,190,373 B1 | 2/2001 | Palermo et al. |
| 5,944,730 | A | 8/1999 | Nobles et al. | 6,193,733 B1 | 2/2001 | Adams |
| 5,951,576 | A | 9/1999 | Wakabayashi | 6,193,734 B1 | 2/2001 | Bolduc et al. |
| 5,951,600 | A | 9/1999 | Lemelson | 6,197,037 B1 | 3/2001 | Hair |
| 5,954,732 | A | 9/1999 | Hart et al. | 6,217,611 B1 | 4/2001 | Klostermeyer |
| 5,954,735 | A | 9/1999 | Rygaard | 6,221,083 B1 | 4/2001 | Mayer |
| 5,957,363 | A | 9/1999 | Heck | 6,241,738 B1 | 6/2001 | Dereume |
| 5,957,938 | A | 9/1999 | Zhu et al. | 6,241,741 B1 | 6/2001 | Duhaylongsod et al. |
| 5,957,940 | A | 9/1999 | Tanner et al. | 6,248,117 B1 | 6/2001 | Blatter |
| 5,961,481 | A | 10/1999 | Sterman et al. | 6,250,308 B1 | 6/2001 | Cox |
| 5,961,539 | A | 10/1999 | Northrup, III et al. | 6,254,615 B1 | 7/2001 | Bolduc et al. |
| 5,964,772 | A | 10/1999 | Bolduc et al. | 6,269,819 B1 | 8/2001 | Oz et al. |
| 5,964,782 | A | 10/1999 | Lafontaine et al. | 6,280,457 B1 * | 8/2001 | Wallace et al. ............... 606/200 |
| 5,972,004 | A | 10/1999 | Williamson, IV et al. | 6,280,460 B1 | 8/2001 | Bolduc et al. |
| 5,972,024 | A | 10/1999 | Northrup, III et al. | 6,283,979 B1 | 9/2001 | Mers Kelly et al. |
| 5,976,159 | A | 11/1999 | Bolduc et al. | 6,283,993 B1 | 9/2001 | Cosgrove et al. |
| 5,976,161 | A | 11/1999 | Kirsch et al. | 6,296,622 B1 | 10/2001 | Kurz et al. |
| 5,976,164 | A | 11/1999 | Bencini et al. | 6,296,656 B1 | 10/2001 | Bolduc et al. |
| 5,976,178 | A | 11/1999 | Goldsteen et al. | 6,306,141 B1 | 10/2001 | Jervis |
| 5,984,917 | A | 11/1999 | Fleischman et al. | 6,332,893 B1 | 12/2001 | Mortier et al. |
| 5,984,959 | A | 11/1999 | Robertson et al. | 6,346,074 B1 | 2/2002 | Roth |
| 5,989,242 | A | 11/1999 | Saadat et al. | 6,346,112 B2 | 2/2002 | Adams |
| 5,989,268 | A | 11/1999 | Pugsley, Jr. et al. | 6,350,269 B1 | 2/2002 | Shipp et al. |
| 5,989,276 | A | 11/1999 | Houser et al. | 6,352,543 B1 | 3/2002 | Cole |
| 5,989,278 | A | 11/1999 | Mueller | 6,358,258 B1 | 3/2002 | Arcia et al. |
| 5,989,465 | A | 11/1999 | Shipp et al. | 6,361,559 B1 | 3/2002 | Houser et al. |
| 5,993,468 | A | 11/1999 | Rygaard | 6,368,348 B1 | 4/2002 | Gabbay |
| 5,997,556 | A | 12/1999 | Tanner | 6,371,964 B1 | 4/2002 | Vargas et al. |
| 6,001,110 | A | 12/1999 | Adams | 6,387,105 B1 | 5/2002 | Gifford, III et al. |

| | | |
|---|---|---|
| 6,391,038 B2 | 5/2002 | Vargas et al. |
| 6,402,764 B1 | 6/2002 | Hendricksen et al. |
| 6,406,492 B1 | 6/2002 | Lytle |
| 6,406,493 B1 | 6/2002 | Tu et al. |
| 6,409,739 B1 | 6/2002 | Nobles et al. |
| 6,409,758 B2 | 6/2002 | Stobie et al. |
| 6,416,527 B1 | 7/2002 | Berg et al. |
| 6,418,597 B1 | 7/2002 | Deschenes et al. |
| 6,419,658 B1 | 7/2002 | Restelli et al. |
| 6,419,681 B1 | 7/2002 | Vargas et al. |
| 6,419,695 B1 | 7/2002 | Gabbay |
| 6,425,900 B1 | 7/2002 | Knodel et al. |
| 6,428,550 B1 | 8/2002 | Vargas et al. |
| 6,428,555 B1 | 8/2002 | Koster, Jr. |
| 6,451,048 B1 | 9/2002 | Berg et al. |
| 6,461,320 B1 | 10/2002 | Yencho et al. |
| 6,475,222 B1 | 11/2002 | Berg et al. |
| 6,478,804 B2 | 11/2002 | Vargas et al. |
| 6,485,496 B1 | 11/2002 | Suyker et al. |
| 6,491,707 B2 | 12/2002 | Makower et al. |
| 6,497,671 B2 * | 12/2002 | Ferrera et al. ............... 623/1.18 |
| 6,497,710 B2 | 12/2002 | Yencho et al. |
| 6,514,265 B2 | 2/2003 | Ho et al. |
| 6,517,558 B2 | 2/2003 | Gittings et al. |
| 6,524,338 B1 | 2/2003 | Gundry |
| 6,533,812 B2 | 3/2003 | Swanson et al. |
| 6,537,248 B2 | 3/2003 | Mulier et al. |
| 6,537,288 B2 | 3/2003 | Vargas et al. |
| 6,547,799 B2 | 4/2003 | Hess et al. |
| 6,551,332 B1 * | 4/2003 | Nguyen et al. ............... 606/151 |
| 6,562,053 B2 | 5/2003 | Schulze et al. |
| 6,575,985 B2 | 6/2003 | Knight et al. |
| 6,589,255 B2 | 7/2003 | Schulze et al. |
| 6,607,541 B1 | 8/2003 | Gardiner et al. |
| 6,607,542 B1 | 8/2003 | Wild et al. |
| 6,613,059 B2 | 9/2003 | Schaller et al. |
| 6,629,988 B2 | 10/2003 | Weadock |
| 6,635,214 B2 | 10/2003 | Rapacki et al. |
| 6,641,593 B1 | 11/2003 | Schaller et al. |
| 6,648,900 B2 | 11/2003 | Fleischman et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,541 B1 | 11/2003 | Vargas et al. |
| 6,660,015 B1 | 12/2003 | Berg et al. |
| 6,682,540 B1 | 1/2004 | Sancoff et al. |
| 6,695,859 B1 | 2/2004 | Golden et al. |
| 6,702,826 B2 | 3/2004 | Liddicoat et al. |
| 6,709,442 B2 | 3/2004 | Miller et al. |
| 6,712,829 B2 | 3/2004 | Schulze |
| 6,719,768 B1 | 4/2004 | Cole et al. |
| 6,743,243 B1 | 6/2004 | Roy et al. |
| 6,749,622 B2 | 6/2004 | McGuckin et al. |
| 6,776,782 B2 | 8/2004 | Schulze |
| 6,776,784 B2 | 8/2004 | Ginn |
| 6,776,785 B1 | 8/2004 | Yencho et al. |
| 6,802,847 B1 | 10/2004 | Carson et al. |
| 6,821,286 B1 | 11/2004 | Carranza et al. |
| 6,869,444 B2 | 3/2005 | Gabbay |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,955,679 B1 | 10/2005 | Hendricksen et al. |
| 6,960,221 B2 | 11/2005 | Ho et al. |
| 6,979,337 B2 | 12/2005 | Kato |
| 6,979,338 B1 | 12/2005 | Loshakove et al. |
| 7,022,131 B1 | 4/2006 | Derowe et al. |
| 7,056,330 B2 | 6/2006 | Gayton |
| 7,063,711 B1 | 6/2006 | Loshakove et al. |
| 7,070,618 B2 | 7/2006 | Streeter |
| 7,104,949 B2 | 9/2006 | Anderson et al. |
| 7,182,769 B2 | 2/2007 | Ainsworth et al. |
| 7,220,265 B2 | 5/2007 | Chanduszko et al. |
| 7,220,268 B2 | 5/2007 | Blatter |
| 7,335,212 B2 | 2/2008 | Edoga et al. |
| RE40,377 E | 6/2008 | Williamson, IV et al. |
| 7,547,313 B2 | 6/2009 | Gardiner et al. |
| 7,556,647 B2 | 7/2009 | Drews et al. |
| 7,722,643 B2 | 5/2010 | Schaller et al. |
| 7,744,611 B2 | 6/2010 | Nguyen et al. |
| 7,763,040 B2 | 7/2010 | Schaller et al. |
| 2001/0018592 A1 | 8/2001 | Schaller et al. |
| 2001/0018593 A1 | 8/2001 | Nguyen et al. |
| 2001/0018611 A1 | 8/2001 | Solem et al. |
| 2001/0021856 A1 | 9/2001 | Bolduc et al. |
| 2001/0047181 A1 | 11/2001 | Ho et al. |
| 2002/0010490 A1 | 1/2002 | Schaller et al. |
| 2002/0042623 A1 | 4/2002 | Blatter et al. |
| 2002/0082614 A1 | 6/2002 | Logan et al. |
| 2002/0099395 A1 | 7/2002 | Acampora et al. |
| 2002/0151916 A1 | 10/2002 | Muramatsu et al. |
| 2002/0165561 A1 | 11/2002 | Ainsworth et al. |
| 2002/0173803 A1 | 11/2002 | Ainsworth et al. |
| 2003/0074012 A1 | 4/2003 | Nguyen et al. |
| 2003/0078603 A1 | 4/2003 | Schaller et al. |
| 2003/0083742 A1 | 5/2003 | Spence et al. |
| 2003/0093118 A1 | 5/2003 | Ho et al. |
| 2003/0125755 A1 | 7/2003 | Schaller et al. |
| 2003/0191481 A1 | 10/2003 | Nguyen et al. |
| 2003/0195531 A1 | 10/2003 | Gardiner et al. |
| 2003/0199974 A1 | 10/2003 | Lee et al. |
| 2004/0044406 A1 | 3/2004 | Woolfson et al. |
| 2004/0050393 A1 | 3/2004 | Golden et al. |
| 2004/0068276 A1 | 4/2004 | Golden et al. |
| 2004/0093024 A1 | 5/2004 | Lousararian et al. |
| 2004/0102797 A1 | 5/2004 | Golden et al. |
| 2004/0111099 A1 | 6/2004 | Nguyen et al. |
| 2004/0122514 A1 | 6/2004 | Fogarty et al. |
| 2004/0138685 A1 | 7/2004 | Clague et al. |
| 2004/0167573 A1 | 8/2004 | Williamson, IV et al. |
| 2004/0176663 A1 | 9/2004 | Edoga |
| 2004/0193259 A1 | 9/2004 | Gabbay |
| 2005/0004582 A1 | 1/2005 | Edoga |
| 2005/0021054 A1 | 1/2005 | Ainsworth et al. |
| 2005/0043749 A1 | 2/2005 | Breton et al. |
| 2005/0065601 A1 | 3/2005 | Lee et al. |
| 2005/0070924 A1 | 3/2005 | Schaller et al. |
| 2005/0075659 A1 | 4/2005 | Realyvasquez et al. |
| 2005/0075667 A1 | 4/2005 | Schaller et al. |
| 2005/0080454 A1 | 4/2005 | Drews |
| 2005/0101975 A1 | 5/2005 | Nguyen et al. |
| 2005/0107871 A1 | 5/2005 | Realyvasquez et al. |
| 2005/0131429 A1 | 6/2005 | Ho et al. |
| 2005/0267572 A1 | 12/2005 | Schoon et al. |
| 2006/0004389 A1 | 1/2006 | Nguyen et al. |
| 2006/0122634 A1 | 6/2006 | Ino et al. |
| 2006/0253143 A1 | 11/2006 | Edoga |
| 2006/0271081 A1 | 11/2006 | Realyvasquez |
| 2006/0293701 A1 | 12/2006 | Ainsworth et al. |
| 2007/0010835 A1 | 1/2007 | Breton et al. |
| 2007/0027461 A1 | 2/2007 | Gardiner et al. |
| 2007/0106313 A1 | 5/2007 | Golden et al. |
| 2007/0142848 A1 | 6/2007 | Ainsworth et al. |
| 2007/0150053 A1 | 6/2007 | Gurskis et al. |
| 2008/0119875 A1 | 5/2008 | Ino et al. |
| 2009/0036903 A1 | 2/2009 | Ino et al. |
| 2009/0112233 A1 | 4/2009 | Xiao |
| 2009/0264903 A1 | 10/2009 | Lee et al. |
| 2010/0044410 A1 | 2/2010 | Argentine et al. |

FOREIGN PATENT DOCUMENTS

| | | |
|---|---|---|
| DE | 0377052 | 6/1923 |
| DE | 27 03 529 | 1/1977 |
| DE | 32 03 410 | 5/1981 |
| DE | 32 27 984 | 2/1984 |
| DE | 3504202 | 8/1985 |
| DE | 41 33 800 | 10/1991 |
| DE | 44 02 058 | 4/1995 |
| DE | 195 47 617 | 9/1997 |
| DE | 197 11 288 | 10/1998 |
| DE | 19732234 | 1/1999 |
| EP | 0072232 | 2/1983 |
| EP | 0122046 | 3/1983 |
| EP | 0129441 | 12/1984 |
| EP | 0130037 | 1/1985 |
| EP | 0140557 | 5/1985 |
| EP | 0 121 362 | 9/1987 |
| EP | 0409569 | 1/1991 |
| EP | 0 432 692 | 6/1991 |
| EP | 0 478 949 | 8/1991 |
| EP | 0 494 636 | 7/1992 |
| EP | 0 559 429 | 3/1993 |
| EP | 0598529 | 5/1994 |
| EP | 0 326 426 | 12/1994 |
| EP | 0 419 597 | 12/1994 |
| EP | 0632999 | 1/1995 |
| EP | 0 641 546 | 3/1995 |
| EP | 0656191 | 6/1995 |
| EP | 0687446 | 12/1995 |
| EP | 0705568 | 4/1996 |
| EP | 0 711 532 | 5/1996 |
| EP | 0 734 697 | 10/1996 |
| EP | 0705569 | 10/1996 |
| EP | 0 537 955 | 12/1996 |
| EP | 0 778 005 | 6/1997 |
| EP | 0 815 795 | 1/1998 |
| EP | 0 826 340 | 3/1998 |
| FR | 320 731 | 12/1902 |
| GB | 2 223 410 | 4/1990 |
| JP | 07308322 | 11/1995 |
| JP | 08336544 | 12/1996 |
| JP | 10337291 | 12/1998 |
| RU | 2110222 | 5/1998 |
| SU | 577022 | 10/1977 |
| SU | 1186199 | 10/1985 |
| SU | 1456109 | 2/1989 |
| SU | 1560133 | 4/1990 |
| WO | WO 90/06725 | 6/1990 |
| WO | WO 90/09149 | 8/1990 |
| WO | WO 90/14795 | 12/1990 |
| WO | 91/08708 | 6/1991 |
| WO | WO 91/07916 | 6/1991 |
| WO | WO 91/17712 | 11/1991 |
| WO | WO 92/05828 | 4/1992 |
| WO | 92/12676 | 8/1992 |
| WO | 92/22041 | 12/1992 |
| WO | 93/01750 | 2/1993 |
| WO | WO 94/15535 | 7/1994 |
| WO | WO 94/15537 | 7/1994 |
| WO | WO 96/00035 | 1/1996 |
| WO | WO 96/06565 | 3/1996 |
| WO | WO 96/38090 | 12/1996 |
| WO | 97/12555 | 4/1997 |
| WO | 97/16122 | 5/1997 |
| WO | 97/27898 | 8/1997 |
| WO | WO 97/28744 | 8/1997 |
| WO | 97/31575 | 9/1997 |
| WO | WO 97/32526 | 9/1997 |
| WO | 97/40754 | 11/1997 |
| WO | WO 97/42881 | 11/1997 |
| WO | 98/19636 | 5/1998 |
| WO | WO 98/30153 | 7/1998 |
| WO | WO 98/42262 | 10/1998 |
| WO | 98/48707 | 11/1998 |
| WO | 98/52475 | 11/1998 |
| WO | 99/07294 | 2/1999 |
| WO | 99/12484 | 3/1999 |
| WO | 99/15088 | 4/1999 |
| WO | 99/37218 | 7/1999 |
| WO | 99/62408 | 12/1999 |
| WO | 99/62409 | 12/1999 |
| WO | 99/62415 | 12/1999 |
| WO | 99/63910 | 12/1999 |
| WO | WO 99/62406 | 12/1999 |
| WO | WO 99/62409 | 12/1999 |
| WO | 00/03759 | 1/2000 |
| WO | 00/15144 | 3/2000 |
| WO | 00/44311 | 8/2000 |
| WO | 00/59380 | 10/2000 |
| WO | 00/60995 | 10/2000 |
| WO | 00/64381 | 11/2000 |
| WO | 00/74603 | 12/2000 |
| WO | 01/10310 | 2/2001 |
| WO | 01/19292 | 3/2001 |
| WO | 01/26557 | 4/2001 |
| WO | 01/26586 | 4/2001 |
| WO | 01/28432 | 4/2001 |
| WO | 01/54618 | 8/2001 |
| WO | 01/74254 | 10/2001 |
| WO | 01/82840 | 11/2001 |
| WO | 02/13702 | 2/2002 |
| WO | WO 02/13701 | 2/2002 |
| WO | 02/30295 | 4/2002 |
| WO | 02/30298 | 4/2002 |
| WO | 02/34143 | 5/2002 |
| WO | 02/080779 | 10/2002 |
| WO | 02/080780 | 10/2002 |
| WO | 02/087425 | 11/2002 |
| WO | 03/053289 | 7/2003 |
| WO | 03/088875 | 10/2003 |
| WO | 2005/011468 | 2/2005 |
| WO | 2005/041784 | 5/2005 |
| WO | 2005/058170 | 6/2005 |
| WO | 2006/060594 | 6/2006 |
| WO | 2007/067942 | 2/2007 |
| WO | 2009/137517 | 11/2009 |

OTHER PUBLICATIONS

Grondin, et al., Carpentier's Annulus and De Vega's Annuloplasty: The end of the tricuspid challenge, Nov. 1975, vol. 70, pp. 852-861.
Holper, et al., Surgery for Tricuspid Insufficiency: Long Term Follow-Up After De Vega Annuloplasty, Thorac Cardiovasc Surgeon, 41, 1993.
Maisano, et al., The Double Orifice Technique as a Standardized Approach to Treat Mitral Regurgitation Due to Severe Myxomatous Disease: Surgical Technique, European Journal of Cardiothoracic Surgery, vol. 17, 2000, 201-205.
Rabago, et al., The New De Vega Technique in Tricuspid Annuloplasty: Results in 150 patients, J. Cardiovas Surg. 1980, 21 pp. 231-238.
Rivera, et al., Carpentier's Flexible Ring Versus De Vega's Annuloplasty, J Thorac Cardiovas Surg, Feb. 1985, 89 pp. 196-203.
Wei, et al., De Vega's Semicircular Annuloplasty for Tricuspid Valve Regurgitation, Ann Thorac Surg, 1993, 55: pp. 482-485.
Wylie, et al., Manual of Vascular Surgery, R. H. Egdahl ed. Spring-Verlag: New York, vol. II, 1986, Table of Contents only.
Wylie, et al., Manual of Vascular Surgery, Springer-Verlag New York, vol. I, 1980, Table of Contents only.
Yun, et al. Mitral Valve Replacement, Mastery of Cardiothoracic Surgery, Lippencott-Raven Publishers, 1998, Chapter 34, pp. 329-341.
International Search Report PCT/US98/00462.
International Search Report PCT/US98/00795.
International Search Report PCT/US98/14211.

International Search Report PCT/US99/12563.
International Search Report PCT/US99/12566.
International Search Report PCT/US00/09092.
International Search Report PCT/US01/10501.
International Search Report PCT/US01/31709.
International Search Report PCT/US01/42653.
International Search Report PCT/US02/10865.
International Search Report PCT/US02/10866.
International Search Report PCT/US02/14261.
International Search Report PCT/US03/12073.
International Preliminary Examination Report PCT/US98/00462.
International Preliminary Examination Report PCT/US98/00795.
International Preliminary Examination Report PCT/US99/12566.
International Preliminary Examination Report PCT/US00/09092.
International Preliminary Examination Report PCT/US01/31709.
International Preliminary Examination Report PCT/US01/42653.
International Preliminary Examination Report PCT/US02/14261.
International Preliminary Examination Report PCT/US02/10865.
International Preliminary Examination Report PCT/US02/10866.
International Preliminary Examination Report PCT/US03/12073.
Written Opinion PCT/US99/12563.
Written Opinion PCT/US99/12566.
Written Opinion PCT/US00/09092.
Written Opinion PCT/US01/10501.
Written Opinion PCT/US01/31709.
Written Opinion PCT/US02/10866.
Written Opinion PCT/US02/14261.
Written Opinion PCT/US03/12073.
International Preliminary Report on Patentability PCT/US2004/023728.
Emery et al. "Suture Techniques for MIDCAB Surgery" Chapt. 12, pp. 87-91, May 1997.
Wylie, Edwin J. et al., Manual of Vascular Surgery, (Springer-Verlag New York), 1980 Table of Contents only.
"VCS Clip Applier System," published in 1995 by Auto Suture Company, a Division of U.S. Surgical Corporation (8 pages).

* cited by examiner

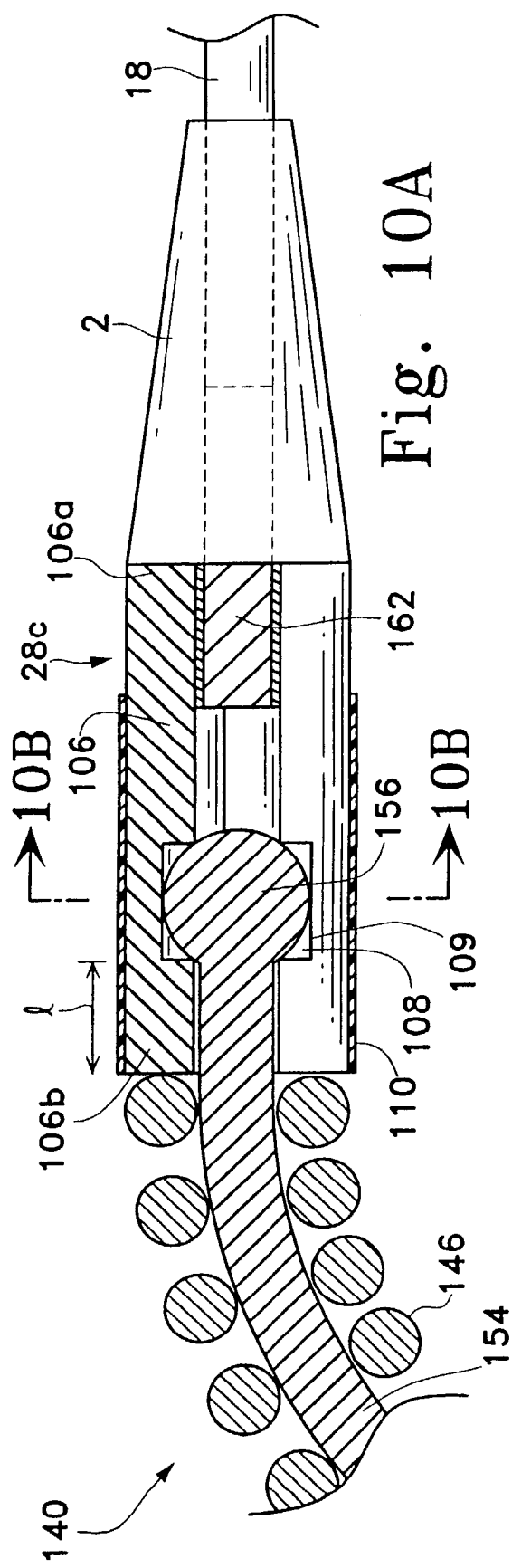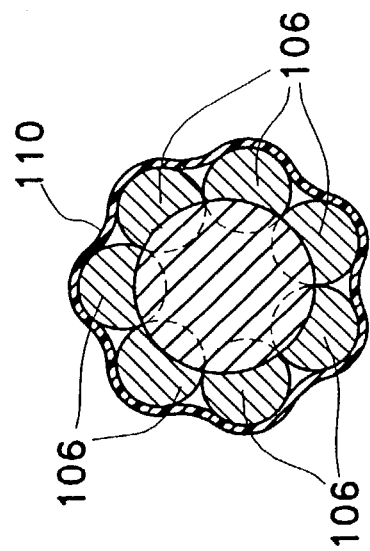
Fig. 10A
Fig. 10B

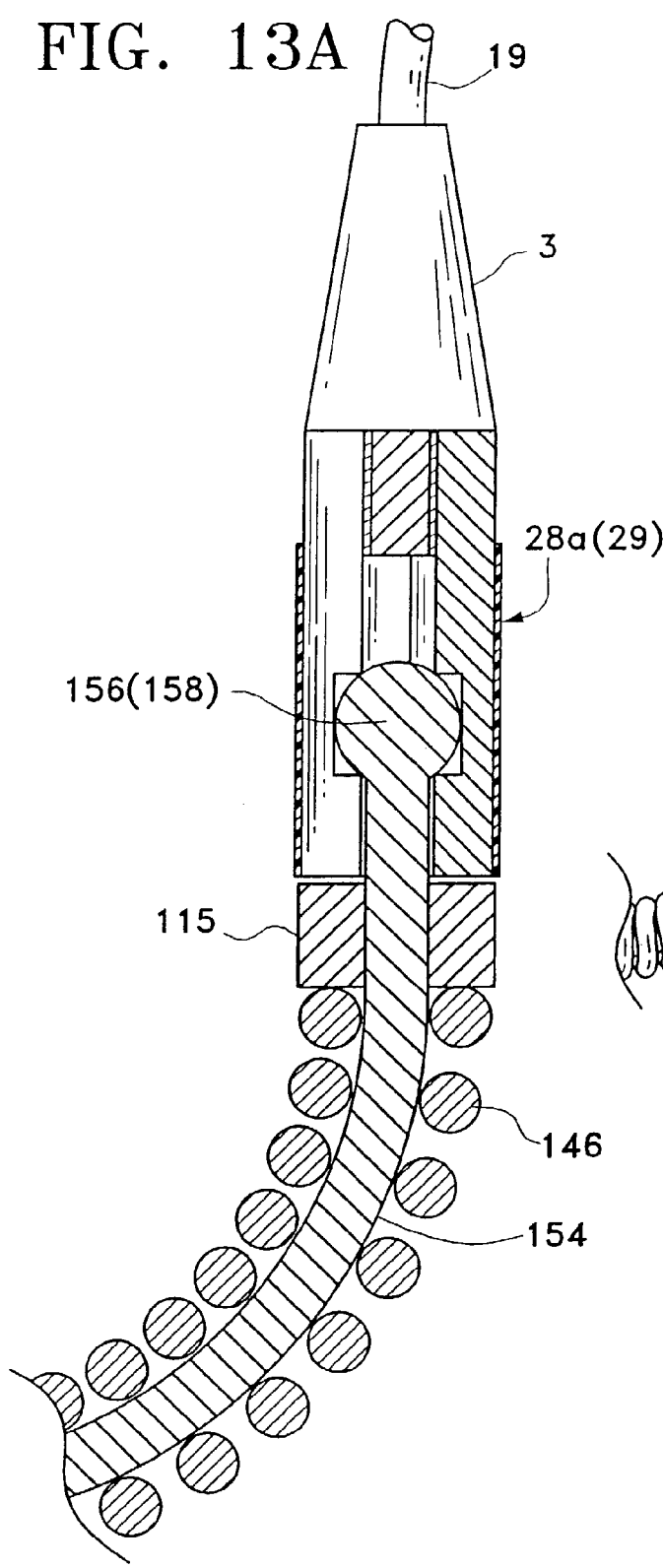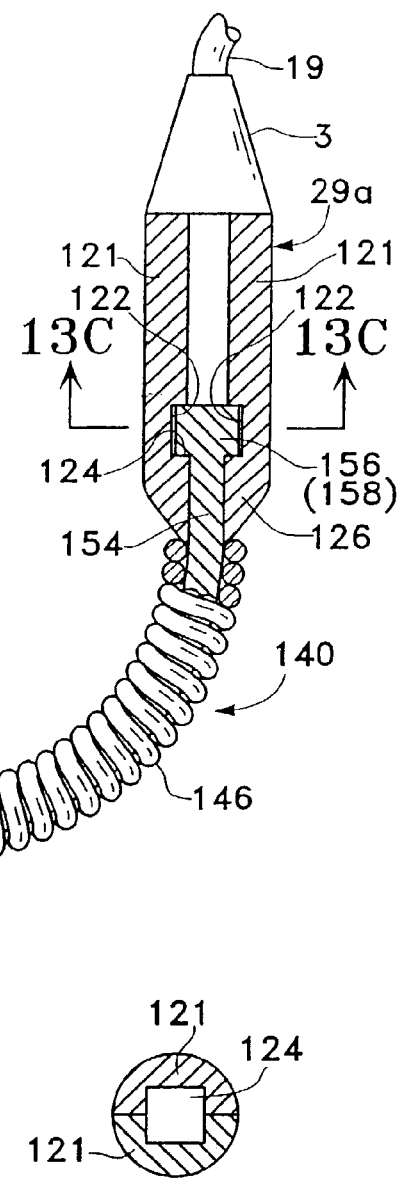
FIG. 13A    FIG. 13B
FIG. 13C

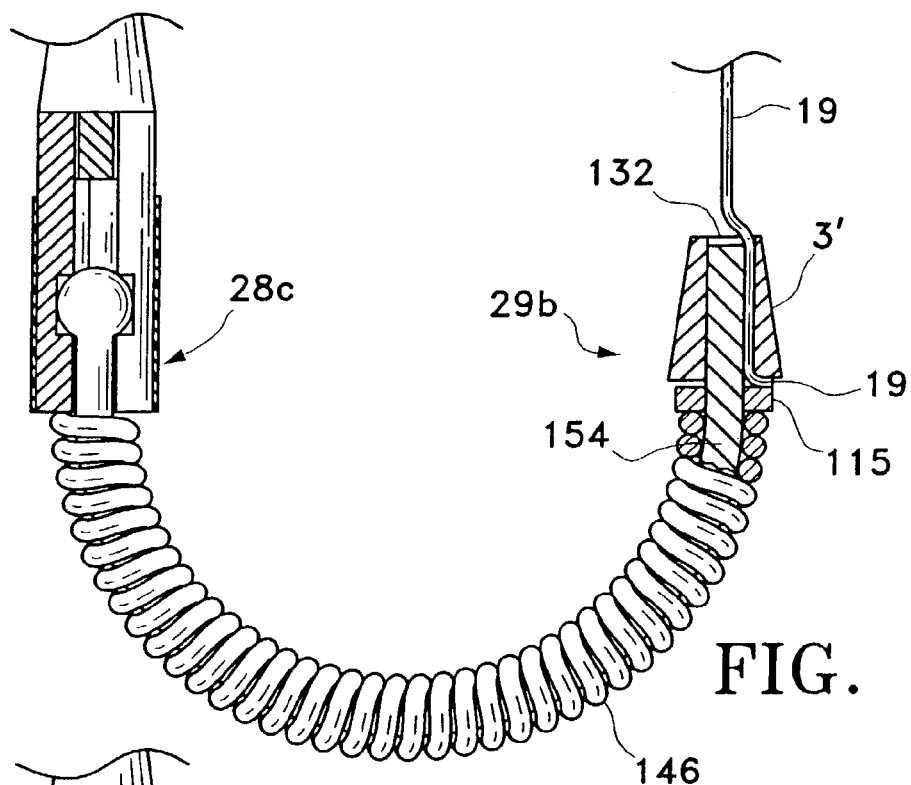
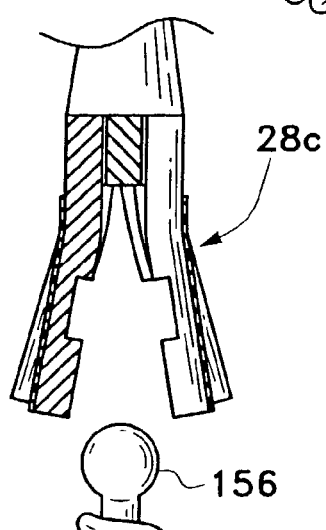
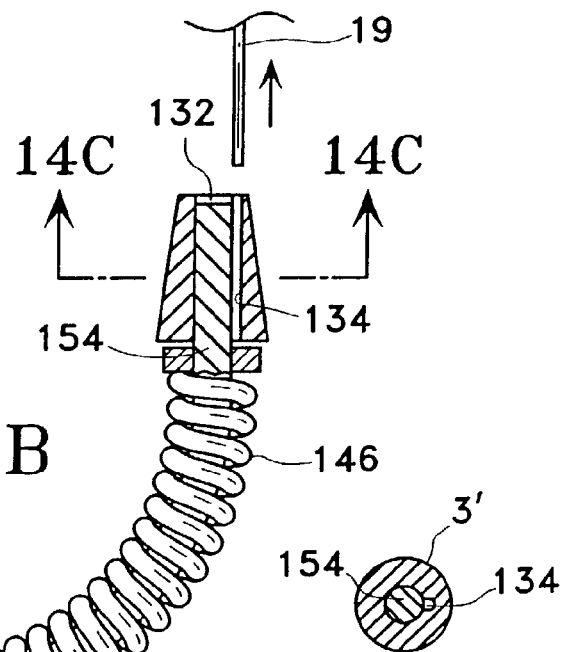
FIG. 14A
FIG. 14B
FIG. 14C

MULTIPLE BIAS SURGICAL FASTENER

CROSS REFERENCE TO RELATED APPLICATION(S)

This application is a continuation of U.S. patent application Ser. No. 09/541,397, entitled Multiple Bias Surgical Fastener and filed Mar. 31, 2000, which application is incorporated by reference in its entirety and to which we claim priority under 35 U.S.C. §120.

TECHNICAL FIELD

The present invention relates to surgical fasteners for connecting body tissues, tissue and prostheses, tissue and graft or any combination thereof.

BACKGROUND

Minimally invasive surgery has allowed physicians to carry out many surgical procedures with less pain and disability than conventional, open surgery. In performing minimally invasive surgery, the surgeon makes a number of small incisions through the body wall to obtain access to the tissues requiring treatment. Typically, a trocar is delivered into the body with a cannula. After the trocar pierces into the body cavity, it is removed and the cannula is left with one end in the body cavity.

When a minimally invasive procedure is done in the abdominal cavity, the retroperitoneal space, or chest, the space in which the operation is performed is more limited, and the exposure to the involved organs is more restricted, than with open surgery. Moreover, in a minimally invasive procedure, the instruments used to assist with the operation are passed into the surgical field through cannulae. When manipulating instruments through cannulae, it is extremely difficult to position tissues in their proper alignment with respect to each other, pass a needle through the tissues, form a knot with the suture material once the tissues are aligned, and prevent the suture material from becoming tangled.

The fastening of body tissues together, or of fastening body tissues to graft materials becomes much more difficult in the restricted spaces imposed upon a surgeon when working through cannulae. Because the use of sutures is often difficult if not impossible in these situations, various other forms of fasteners have been developed to simplify the joining together of tissues and tissues with grafts in these environments, as well as in more conventional surgical procedures.

One variation of a suture is disclosed in U.S. Pat. No. 5,002,563, which forms surgical sutures from shape memory alloys. A suture is formed in the shape of a loop and a needle is affixed to an end thereof. A straight sleeve is provided to maintain the suture relatively straight as it is being inserted into the tissues to be joined. Removal of the sleeve allows the suture to return to its memorized loop shape. End segments of the loop can then be interlocked manually to secure the wound closure. Although this device is less cumbersome than tying conventional sutures, it still requires a coordinated effort to advance the suture into the tissues while removing the sleeve during the insertion process. Also, the interlocking step is similar to suturing, if not as difficult or complicated as tying a conventional suture. This device is disclosed for use in closure of deep wounds and there is no suggestion of use in close environments such as in minimally invasive surgical procedures.

PCT publication nos. WO 99/62406 and WO 99/62409, which are commonly assigned to the assignee of the present application, disclose tissue connector assemblies having a clip movable between an open state and a closed state and a mechanical restraining device attached to the clip for restraining the clip in its open state. The clip has a generally U-shaped configuration when in its open state. A needle may be releasably attached to the clip. This type of tissue connector assembly is discussed further below, with regard to FIGS. 4 and 5. PCT publication nos. WO 99/62406 and WO 99/62409 are incorporated herein, by reference thereto, in their entireties.

SUMMARY OF THE INVENTION

The present invention involves surgical fasteners having biasing members which aid in the closure of the fasteners, and methods of making such fasteners. A fastener, according to the present invention, includes a clip movable between an open configuration and a closed configuration, and a biasing member contacting the clip and biased to conform to the closed configuration when in a free state. The biasing member may be applied to form an integrated system with the clip, such that the biasing member and clip actuate in concert to close the fastener, thereby providing an optimal fastener configuration exhibiting an optimal closing force.

Additionally, the clip is biased to conform to the closed configuration when in a free state. The clip may comprise a wire having a shape memory which defines a closed configuration, which may be substantially spiral-shaped, or another shape.

The biasing member may comprise a coil surrounding at least a portion of the clip, and may be a double coil. The biasing member may reside between two restraints located on the clip. Further, a release mechanism may be provided which is adapted to engage the clip at at least one of the restraints and to bias the biasing member to force the clip into the open configuration.

A method of making a surgical fastener according to the present invention includes winding a clip, formed of a shape memory material, into a predetermined closed configuration; setting the clip into the predetermined closed configuration so that the clip has a memory configuration which is the predetermined closed configuration; and conforming a biasing member to the clip in the predetermined closed configuration; setting the clip and biasing member into the predetermined closed configuration to form a fastener comprising the clip and the biasing member wherein each has a memory configuration which is the predetermined closed configuration.

The clip and biasing member may each be set by heating at a predetermined temperature for a predetermined time, and the combination of these components may further be set by heating at a predetermined temperature for a predetermined time.

BRIEF DESCRIPTION OF THE DRAWINGS

FIGS. 10A and 10B are sectional views of a fastener release mechanism, which may be used in the assembly of FIG. 9;

FIG. 13A shows a release mechanism that may be used with the second needle in the assembly of FIG. 12;

FIGS. 13B and 13C show another release mechanism that may be used with the second needle in the assembly of FIG. 12, where FIG. 13C is a sectional view of FIG. 13B taken along line 13C-13C;

FIGS. 14A, B and C show another release mechanism that may be used with the second needle in the assembly of FIG. 12, where FIGS. 14A and 14B are partial sectional views of the system in a coupled and decoupled state, respectively, and FIG. 14C is a transverse cross-sectional view taken along line 14C-14C in FIG. 14B;

FIGS. 15A and 15B are sectional views and FIG. 15C is a top view of the elongated grabber member of FIGS. 15A and 15B;

Corresponding reference characters indicate corresponding parts throughout the several views of the drawings.

DETAILED DESCRIPTION

Figure 4:
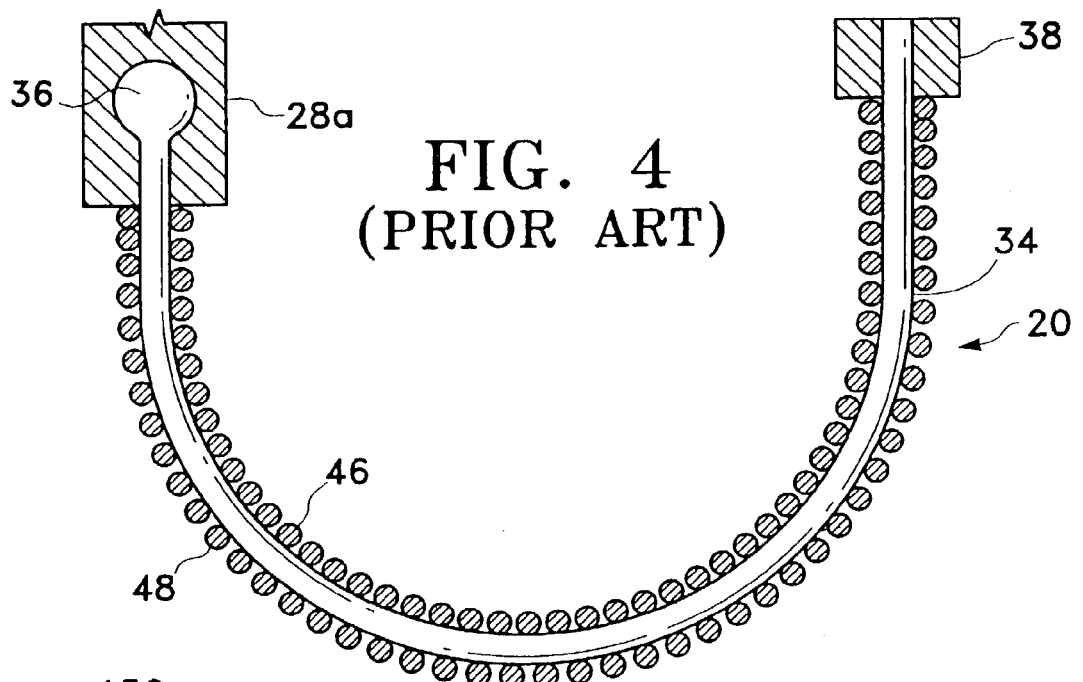
FIG. 4 shows a prior art fastener in an open configuration.

Tissue connectors such as those discussed in PCT publication nos. WO 99/62406 and WO 99/62409, as described above are also disclosed in currently copending and commonly assigned application Ser. No. 09/090,305, filed Jun. 3, 1998, which is incorporated herein, by reference thereto, in its entirety. Referring to FIG. 4, a fastener (e.g., fastener 20) such as that described in application Ser. No. 09/090,305 comprises a deformable wire 34 made of a shape memory alloy. A nickel titanium (e.g., Nitinol) based alloy may be used, for example. The Nitinol may include additional elements which affect the yield strength of the material or the temperature at which particular pseudoelastic or shape transformation characteristics occur. The transformation temperature may be defined as the temperature at which a shape memory alloy finishes transforming from martensite to austenite upon heating (i.e., $A_f$ temperature). The shape memory alloy preferably exhibits pseudoelastic (superelastic) behavior when deformed at a temperature slightly above its transformation temperature. At least a portion of the shape memory alloy is converted from its austenitic phase to its martensitic phase when the wire is in its deformed configuration. As the stress is removed, the material undergoes a martensitic to austenitic conversion and springs back to its original undeformed configuration. When the wire is positioned within the tissue in its undeformed configuration, a residual stress is present to maintain the tissue tightly together. In order for the pseudoelastic wire to retain sufficient compression force in its undeformed configuration, the wire should not be stressed past its yield point in its deformed configuration to allow complete recovery of the wire to its undeformed configuration. The shape memory alloy is preferably selected with a transformation temperature suitable for use with a stopped heart condition where cold cardioplegia has been injected for temporary paralysis of the heart tissue (e.g., temperatures as low as 8-10 degrees Celsius).

It is to be understood that the shape memory alloy may also be heat activated, or a combination of heat activation and pseudoelastic properties may be used, as is well known by those skilled in the art.

Figure 2:
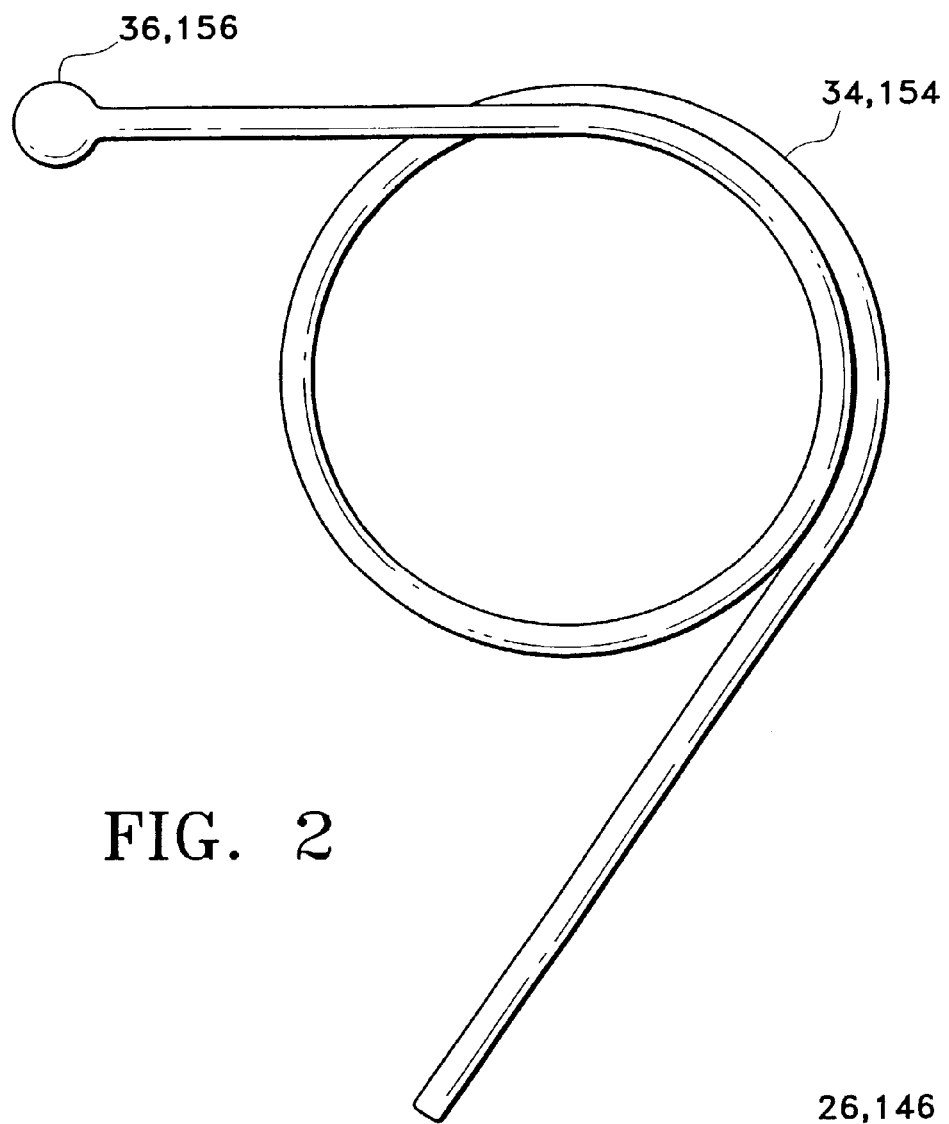
FIG. 2 is a view of a clip, absent of any biasing member, in a closed configuration.
Figure 5:
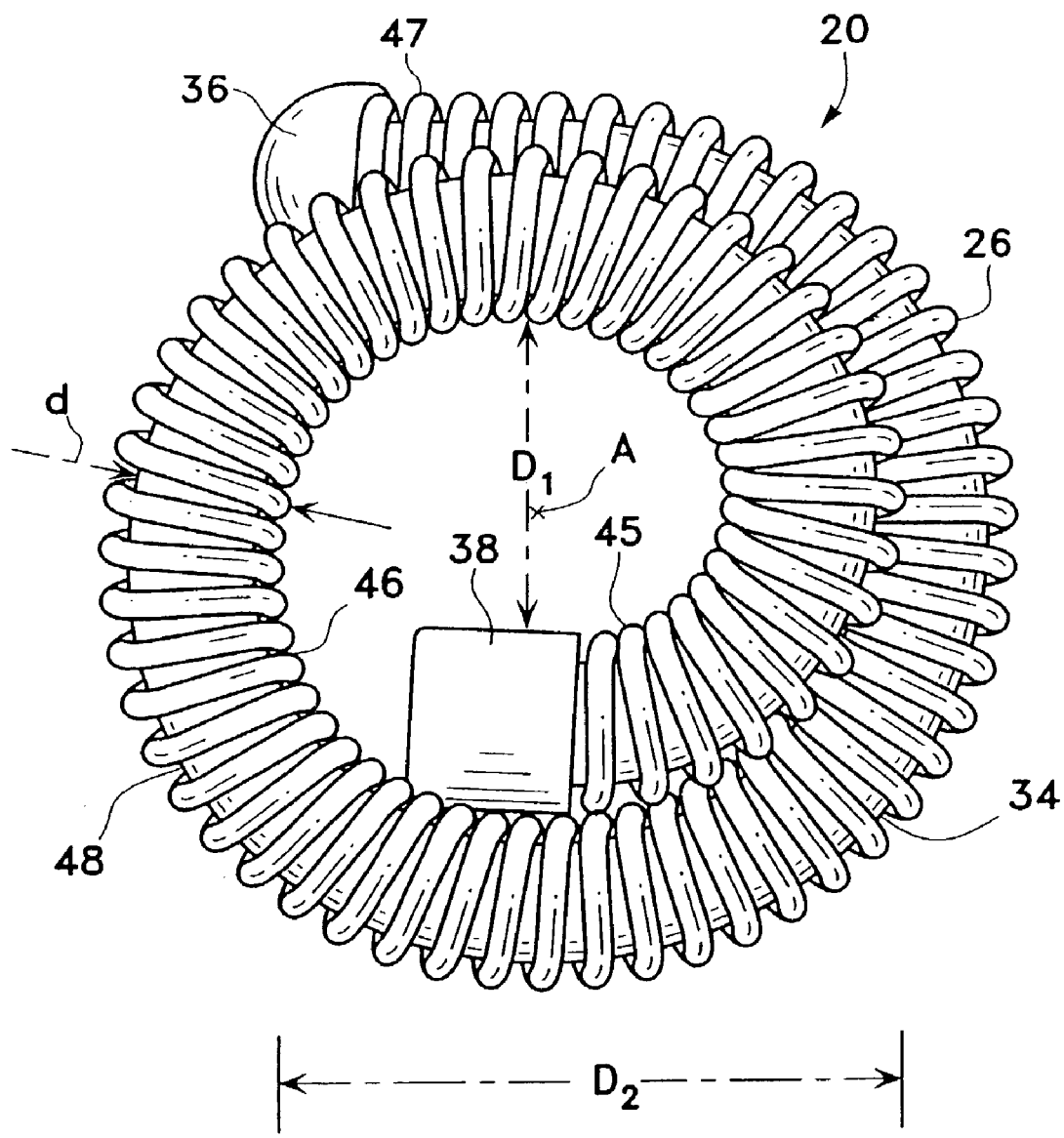
FIG. 5 shows the fastener of FIG. 4 in a closed configuration.

The cross-sectional diameter of the wire and length of the wire will vary depending on the specific application. The diameter "d" of wire 34 may be, for example, between 0.001 and 0.015 inch. For coronary bypass applications, the diameter is preferably between 0.001 and 0.008 inch with a diameter $D_1$ of the loop (FIG. 5) being between 0.0125 and 0.0875 inch. As shown in FIGS. 2 and 5, the wire 34 may have a circular cross-sectional shape and a generally spiral shaped configuration when in a closed position. The diameter $D_1$ of the loop of the fastener 20, with coil 26, in its closed position is preferably sized to prevent movement between adjacent tissues. It is to be understood, however, that the wire may have other cross-sectional shapes such as rectangular, or may be formed from multiple strands.

One end of wire 34, may include an enlarged portion 36 having a cross-sectional area greater than the cross-sectional area of the wire and diameter of the coil to resist the coil from passing thereover. Alternatively, enlarged portion 36 may have a cross-section that allows the coil to be pulled over the enlarged portion. For example, the cross sectional diameter of the enlarged portion may be about equal to the inside diameter of the coil. The enlarged portion 36 also may be provided to cooperate with a release mechanism, which is described in further detail with reference to the present invention below.

In making the fastener 20, the wire 34 is first formed in the generally spiral shaped configuration shown in FIG. 2. The wire 34 may be formed in the above described shape by first wrapping the wire onto a mandrel and heat treating the wire at approximately 400-550 degrees Celsius for approximately 5 to 30 minutes. The wire 34 is then air quenched at room temperature. The mandrel may have a constant diameter or may be conical in shape, to facilitate forming the spiral configuration shown in FIG. 5. Other shapes are possible as described in application Ser. No. 09/090,305. Coil 26 is formed by wrapping a wire around a cylindrical mandrel (not shown) thereby cold-working the wire into a coil shape having a straight axial configuration as shown in FIG. 3. Next, the coil 26 is axially slid over the wire 34 whereupon it takes on the substantially spiral shaped configuration of the wire 34. Next, a locking device such as 28a, for example (FIG. 4) is locked in position over enlarged portion 36. Afterwards, an additional enlarged portion 38 is slid on the wire 34 and driven against the coil 26 to compress the same and open the fastener. When in the open position, the enlarged portion 38 is then fixed to the wire 34 by swedging or equivalent fixation technique. Next, any extension of the wire 34 beyond enlarged portion 38 is removed or cut off from the fastener assembly 20.

When the fastener 20 is in its free state (i.e., with the wire 34 in its undeformed configuration and the coil 26 having substantially no axial compression forces applied to its ends), loops of the coil are generally spaced from one another and do not exert a significant opening force on the wire 34 (FIG. 5). In examples using a platinum coil, there is almost no force applied to the wire 34. Although the force may be negligible, the platinum coil does not assist in the closing of the fastener. In using a more resilient coil, however, since the coil was initially formed in a straight configuration, there may be some amount of residual stress in the coil when it is placed in the substantially spiral configuration and thus some force may be applied to the wire 34 when the fastener is in its free state.

When the spring 26 is compressed (with the wire 34 in its deformed configuration as shown in FIG. 4), loops of the coil on the inner portion 46 of the spring are squeezed together with a tight pitch so that the loops are contiguous with one another while loops on the outer portion 48 of the spring are spaced from one another (FIG. 4). This is due to the compressed inner arc length of the spring 26 and the expanded outer arc length of the spring. The compression of the loops on the inner portion 46 of the spring 26 exerts a force on the inner side of the wire 34 which forces the wire to spread open (i.e., tends to straighten the wire from its closed configuration to its open configuration). The end of the spring 26 adjacent the enlarged portion 38 is held in a fixed position relative to the wire 34. The opposite end of the spring 26 is free to move along the wire 34 and is held in place when the spring is in its compressed position by a locking device or release mechanism 28a.

When the release mechanism 28a is removed from the wire 34 and enlarged portion 36, the spring or coil 26 releases stored energy and expands to abut against the enlarged portion 36 again, which also allows the wire 34 to resume its substantially spiral shaped configuration, thereby also conforming the coil 26 into the substantially spiral-shaped configuration. Because the coil was not originally formed in the substantially spiral-shaped configuration, its tendency, if unaffected by outside forces, would be to return to the straight configuration, or possibly to remain in its present configuration, as in the case of a thin, malleable, platinum coil. Thus, the coil 26, at best, does not aid the wire 34 in returning the fastener 20 to its closed position or free state, and, at worst, actually hinders the wire 34 from returning to the closed position. This further translates to possibly reducing the static closing force of the fastener somewhat.

Figure 1A:
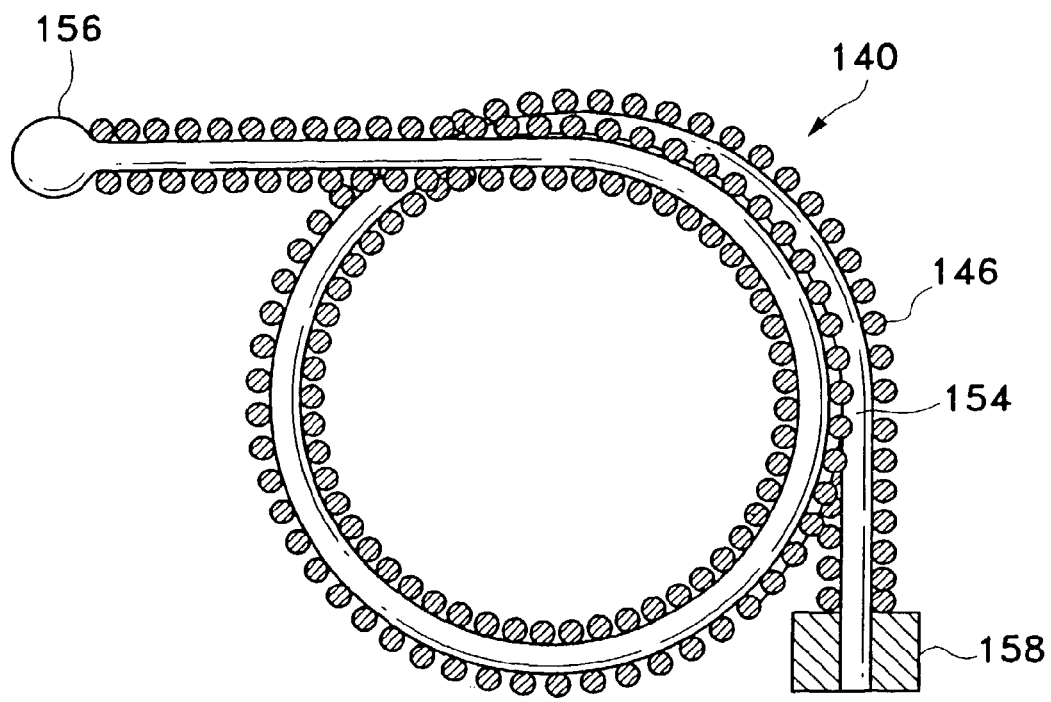
FIG. 1A is a view of a surgical fastener according to the present invention.

In an example according to the present invention, shown in FIG. 1A, a fastener 140 is formed such that the coil 146 assists the wire 154 in its return to the closed state. In this embodiment, the coil 146 forms an integral part of the fastener (i.e., fastening system) so as to assist in the closing thereof. In making the fastener 140, the wire 154 may be first formed in the generally spiral shaped configuration shown in FIG. 2. The wire 154 is wound on a clip fixture, e.g. a tapered shaft (not shown), and is then heat treated, in a first heat cycle, in a convection oven set at a temperature ranging from about 450° C. to less than about 500° C. for a period of about one to twenty minutes, to set the desired shape (e.g., the shape shown in FIG. 2) of the bare clip 154. In one example, the wire is heated in a first heat cycle at a temperature of about 475° C. for about six minutes. The first heat cycle does not fully remove the cold worked stresses in the wire 154, since the first heat cycle is performed below 500° C. Of course, the wire 154 may be formed in various other configurations, some examples of which are described in application serial Ser. No. 09/090,305, the entire contents of which are hereby incorporated by reference thereto. Enlarged portion 156 is formed prior to the first heat cycle of the wire 154, and may be formed by attaching a member to the end of wire 154 by welding, gluing or other suitable attachment means or may be formed integrally with the wire by deforming the end of the wire, such as by heat (melting).

Figure 3A:
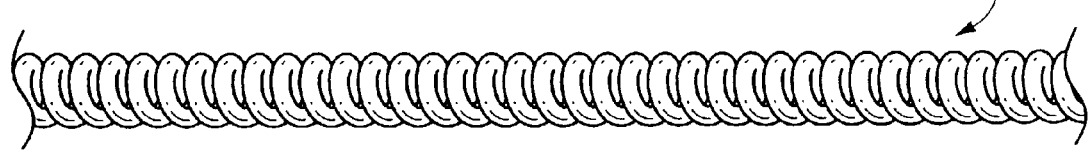
FIG. 3A shows a single coil set in an axially straight configuration.
Figure 3B:
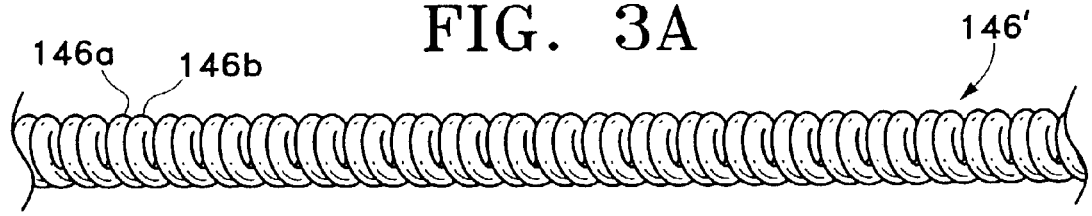
FIG. 3B shows a double coil set in an axially straight configuration.

Coil 146 is formed by first wrapping a wire of shape memory material, such as Nitinol around a cylindrical mandrel (not shown) and then heat setting the wire in a first heat cycle by placing it and the mandrel in a convection oven set at a temperature ranging from about 450° C. to less than about 500° C. for a period of about one to twenty minutes, to set it in an axially straight, configuration such as shown in FIG. 3A. In one example, the coil is heated in a first heat cycle at a temperature of about 475 ° C. for about six minutes. For an even stiffer configuration with correspondingly greater spring recoil, a pair of Nitinol wires (each preferably having about the same length and diameter as wire 146) 146a,146b may be wound side-by-side around the cylindrical mandrel and then heat set in a first heat cycle by placing the pair and the mandrel in a convection oven and heat treating in a first heat cycle according to the parameters described above, to set it in an axially straight, double coil configuration 146', such as shown in FIG. 3B. Of course, other materials which exhibit a sufficient shape memory ability could be substituted for Nitinol, as would be apparent to one of ordinary skill in the art. Also, more than two adjacent wires (e.g., 3, 4 or more) may be wrapped and heat set in a similar procedure.

Figure 6:
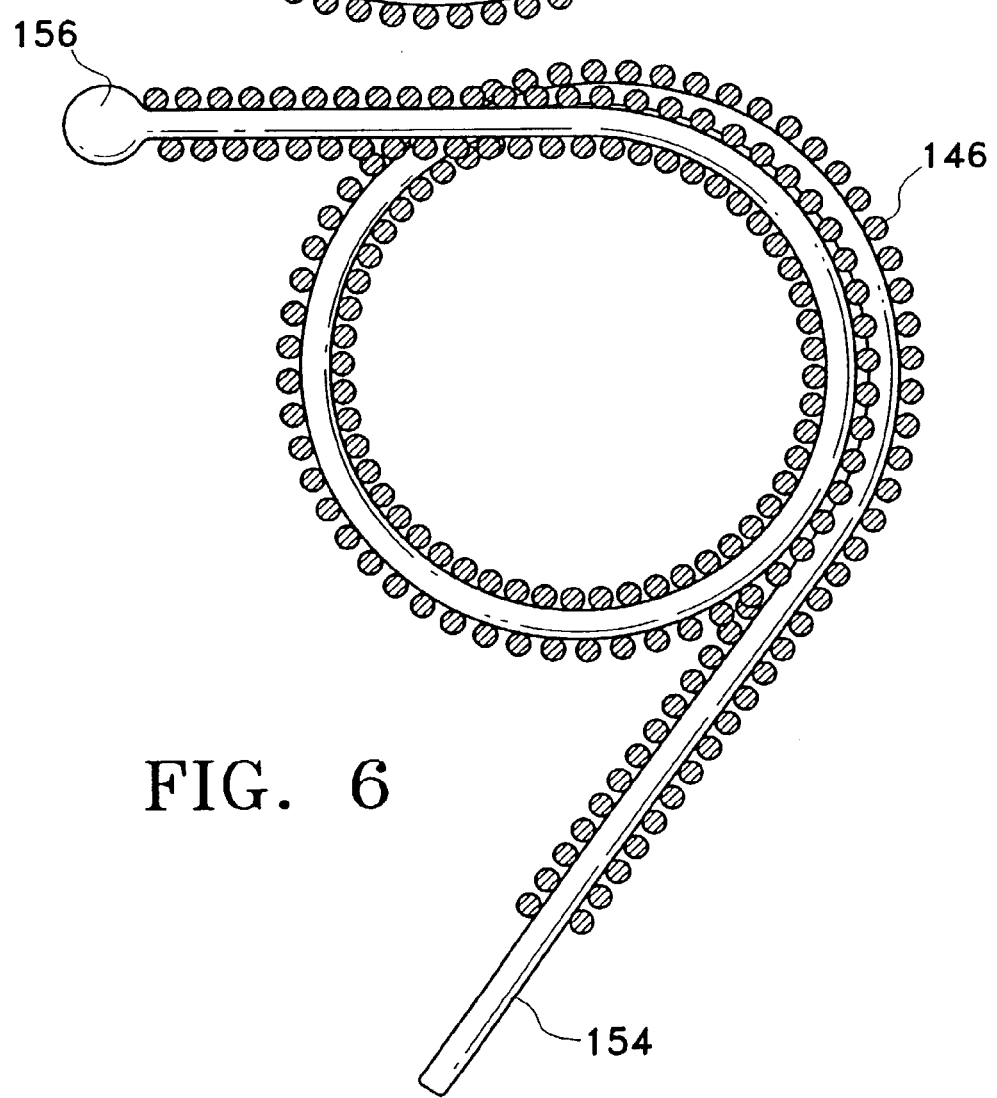
FIG. 6 shows the positioning of a coil over a clip for setting the closed configuration of a fastener.

Next, the coil 146' (or 146, depending on whether a double or single coil (or more) is used) is axially slid over the wire clip 154, such that the leading end of the coil 146' abuts or lies adjacent to the enlarged portion 156, whereupon it takes on the substantially spiral-shaped configuration of the wire 154, as shown in FIG. 6. Once in position on the wire 154, the assembly (wire 154 and coil 146,146') is again heat treated in a second heat cycle, this time in a salt bath, to form an integrated system, wherein the shapes of both components are formed to one another so as to function in concert upon closing of the fastener. The salt bath may be sodium nitrate and potassium nitrate in a 50/50 mixture by weight percent for example. Alternatively, other molten mixtures could be used as would be apparent to those of ordinary skill in the art. The purpose of the salt bath is to provide a much more stable process, with more efficient and constant heat transfer to the entire assembly, thereby optimizing the strength of the fastener by removing any residual cold-worked stress in the materials to optimize the configuration of the fastener.

The salt bath is heated to a temperature of about 500-530° C. and the fastener is submerged therein for a period of about one to six minutes. In one example, the fastener may be submerged in a salt bath having a temperature of about 515° C. for about two minutes. The shape of the coil 146 after treatment in the salt bath cycle, is memory set into the shape of the clip 154, as shown in FIG. 1A, for example, so that each component has a substantially spiral-shaped memory set. Of course, other shapes of the wire 154 could be made initially, as noted above, after which the coil 146 would be processed in the same way as described above, to take on a memory set provided by the shape of the wire 154.

After heat setting as described above, the fastener is assembled with a locking mechanism, much in the same manner as described above with regard to previous embodiments. Although the enlarged portions have been described with spherical and cylindrical configurations, other configurations or configuration combinations can be used. For example, both enlarged portions may be spherical or both may be cylindrical, etc.

Figure 7:
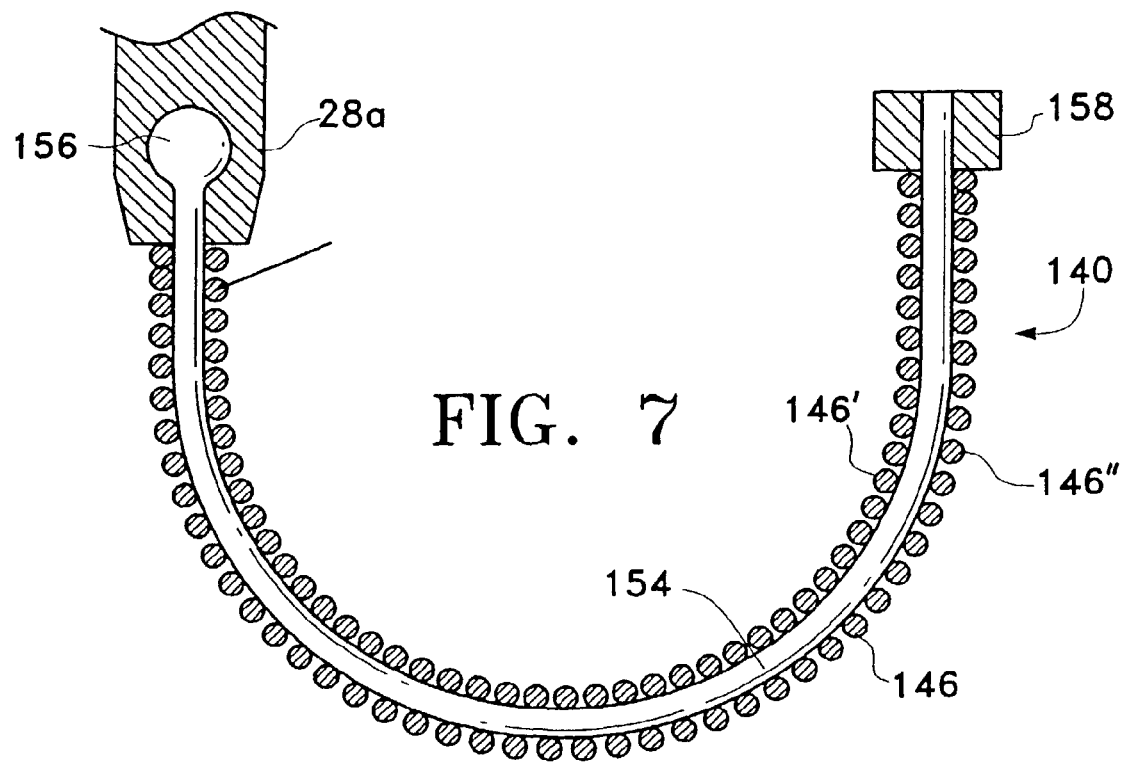
FIG. 7 shows a fastener according to the present invention in an open configuration.

After heat setting the coil 146,146' and wire 154 in the second heat cycle, a locking mechanism, such as 28a for example, is locked in position over the enlarged portion 156. Afterwards, an additional enlarged portion 158 is slid on the wire 154 and driven against the coil 146,146' to compress the same and open the fastener (FIG. 7). While the fastener is in the open position, the enlarged portion 158 is then fixed to the wire 154 by swedging or equivalent fixation technique. Next, any extension of the wire 154 beyond enlarged portion 158 is removed or cut off from the fastener assembly 140. Although enlarged portions 156 and 158 are shown with spherical and cylindrical configurations, other configurations or configuration combinations can be used. For example, both enlarged portions may be spherical or cylindrical, or portion 156 may be cylindrical and portion 158 spherical.

Figure 8:
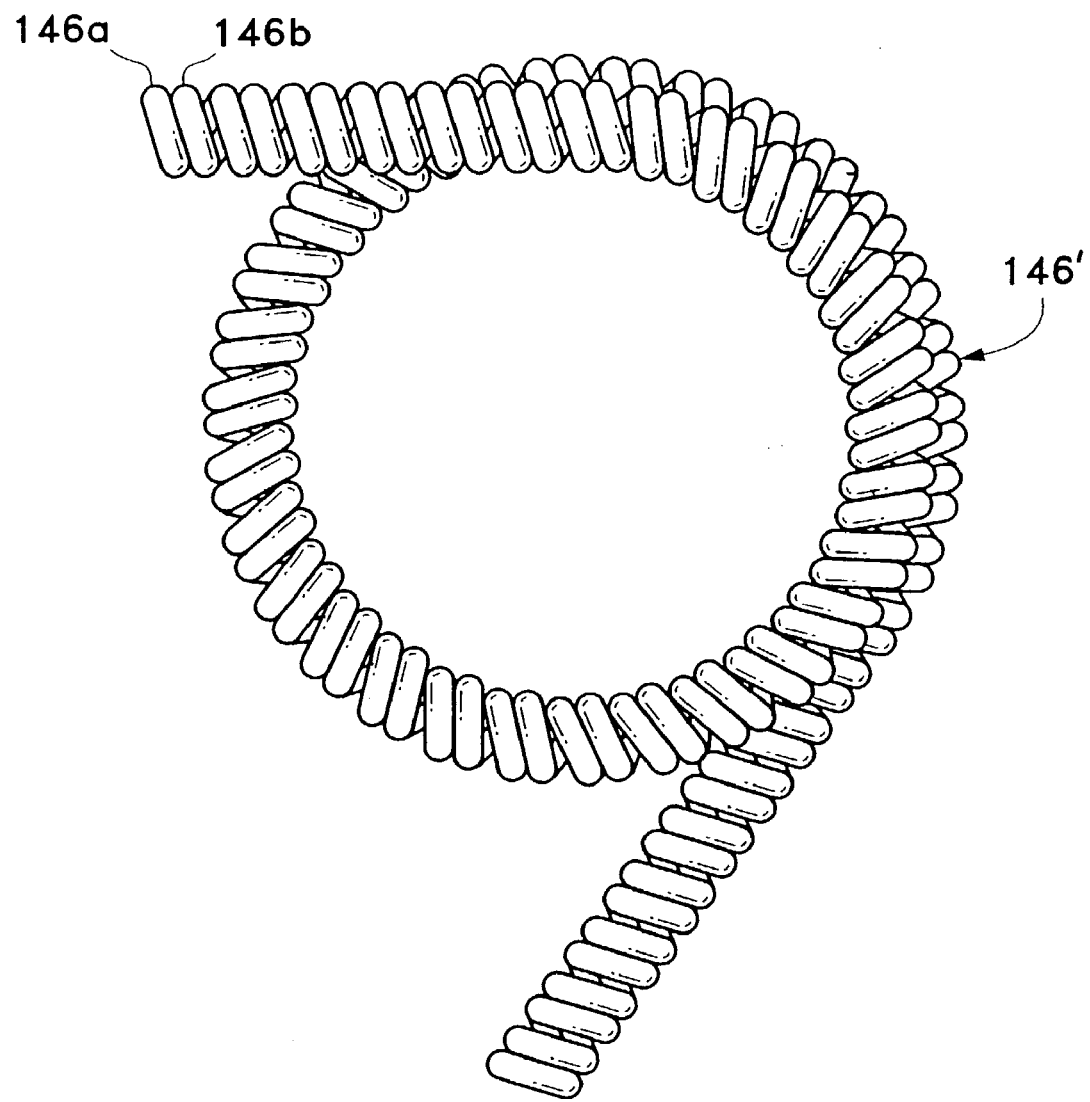
FIG. 8 shows a double coil which is set into a closed configuration.

When the fastener 140 is in its free state (i.e., with the wire 154 in its undeformed configuration and the coil 146 having substantially no axial compression forces applied to its ends), loops of the coil are generally spaced from one another and do not exert a substantial force on the wire 154 (FIG. 1). This is because of the memory set that was fixed in the coil 146 during the preparation of the fastener 140 as described above. Because the memory of the coil 146 has been formed to take on essentially the same configuration as the memory set of the wire 154 when no external forces are applied to the fastener 140, the coil 146 does not "fight against" the closure of the wire 154 as it moves toward its free state. As a further illustration, FIG. 8 shows that even if the coil 146 is removed from the clip 154, it will still assume the general spiral-shaped configuration (or other configuration to which its memory was set while mounted on a wire 154). Thus, the free state of the coil 146 cooperates with the free state of the wire 154.

When the spring 146 is compressed (with the wire 146 in its deformed configuration as shown in FIG. 7), loops of the coil on the inner portion 146' of the spring are squeezed together with a tight pitch so that the loops are contiguous with one another while loops on the outer portion 146" of the spring are spaced from one another (FIG. 7). This is due to the compressed inner arc length of the spring 146 and the expanded outer arc length of the spring. The compression of the loops on the inner portion 146' of the spring 146 exerts a force on the inner side of the wire 154 which forces the wire to spread open (i.e., tends to straighten the wire from its closed configuration to its open configuration). It should be understood, however, that a coil (not shown) having sufficient stiffness, for example, may be used where adjacent loops do not contact one another when the coil is compressed to force wire 154 into an open position. The end of the spring 146 adjacent the enlarged portion 158 is held in a fixed position relative to the wire 154. The opposite end of the spring 146 is free to move along the wire 154 and is held in place when the spring is in its compressed position by a locking device or release mechanism 28a.

When the release mechanism 28a is removed from the wire 154/enlarged portion 156, the spring or coil 146 releases stored energy and expands to again abut against the enlarged portion 156. At the same time, both the coil 146 and the wire 154 move in concert to return to the "free" or closed configuration shown in FIG. 1. Thus, because of the memory set of the coil 146, as well as the wire 154, coil 146 actually assists wire 154 in the closing of the fastener 140 upon removal of the release mechanism 28a.

Referring to FIGS. 1 and 7, fastener 140 is shown in closed and open configurations. When wire 154 is in an undeformed or closed configuration, the fastener is closed (FIG. 1) for keeping or connecting tissue together. When wire 154 is in a deformed or open configuration, the fastener is open (FIG. 7) for insertion of the wire into tissue. As discussed above, wire 154 is in its closed configuration when in a relaxed state, and likewise, coil 146 is in a closed configuration when in a relaxed state. Wire 154 and coil 146 are preferably not deformed past their yield points in the open position. Accordingly, fastener 140 may have a U-shaped configuration in its open position to facilitate insertion of the wire through the tissue. However, other configurations may be used including, but not limited to C-shaped, V-shaped, J-shaped, and other similarly shaped configurations.

The helical wire 154 may have other cross-sectional shapes and be formed of different materials which exhibit shape memory characteristics. Coil 146 is preferably sized so that when in its free (uncompressed state) it extends the length of wire 154 with one end adjacent to enlarged portion 156 and the other end adjacent to enlarged portion 158. It is to be understood that the coil may not extend the full length of the wire. For example, a flange or similar device may be provided on an intermediate portion of wire 154 to limit movement of the coil along the length of the wire.

In addition to the configuration shown in FIG. 5 and the alternative configurations taught in application Ser. Nos. 09/090,305; 09/259,205; 09/089,884; and 09/260,623; all of which are incorporated herein in their entireties by reference thereto, a fastener according to the present invention can be formed in still other configurations. One or both ends of the fastener may extend in a substantially straight direction from the curved form of the wire 154. The straight sections of extensions may extend for a length equal to about two to three times the outside diameter of the coil 146 (as compared to the diameter of the loop) or about 0.010 to 0.020 inches. These extensions may allow the release mechanisms (discussed in detail below) to operate more efficiently and also may simplify manufacture of the fastener.

The fastener may be embodied by a wire (a small clip), having a cross-sectional thickness of about 0.0035 inches, which, similar to the closed configuration of the prior art fastener shown in FIG. 5, forms an inner loop having a diameter $D_1$ of about 0.017 inches and an outer loop dimension $D_2$ (horizontally measured from inside of the loop) of about 0.021 inches. In the open configuration, the exemplary clip may form a U-shape with a depth of the U-shape being about 0.032 inch (0.8 mm).

Figure 1B:
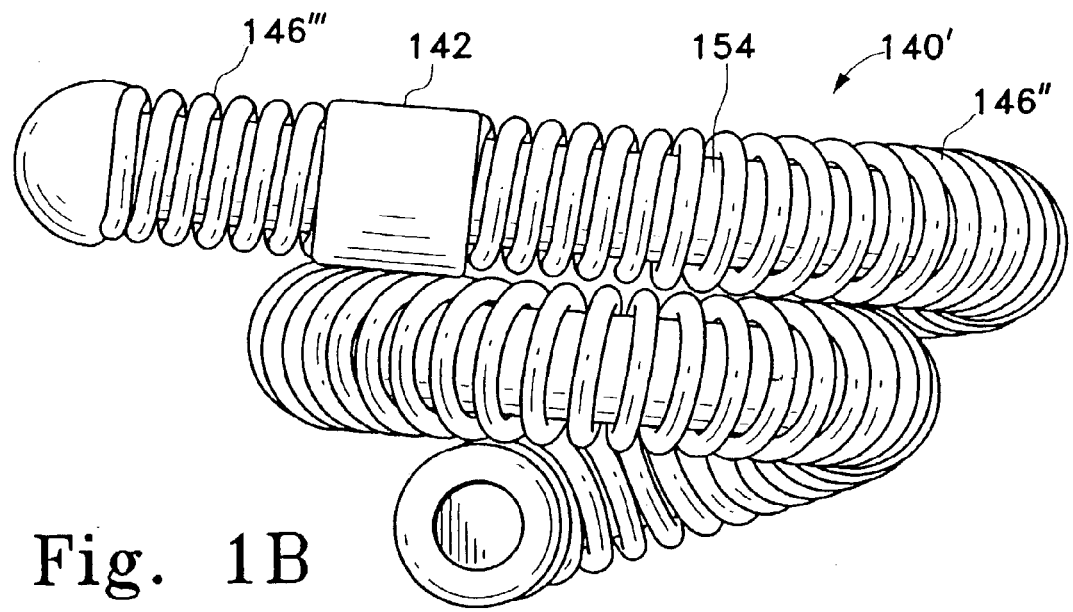
FIGS. 1B and 1C show a variation of the fastener of FIG. 1A.
Figure 1C:
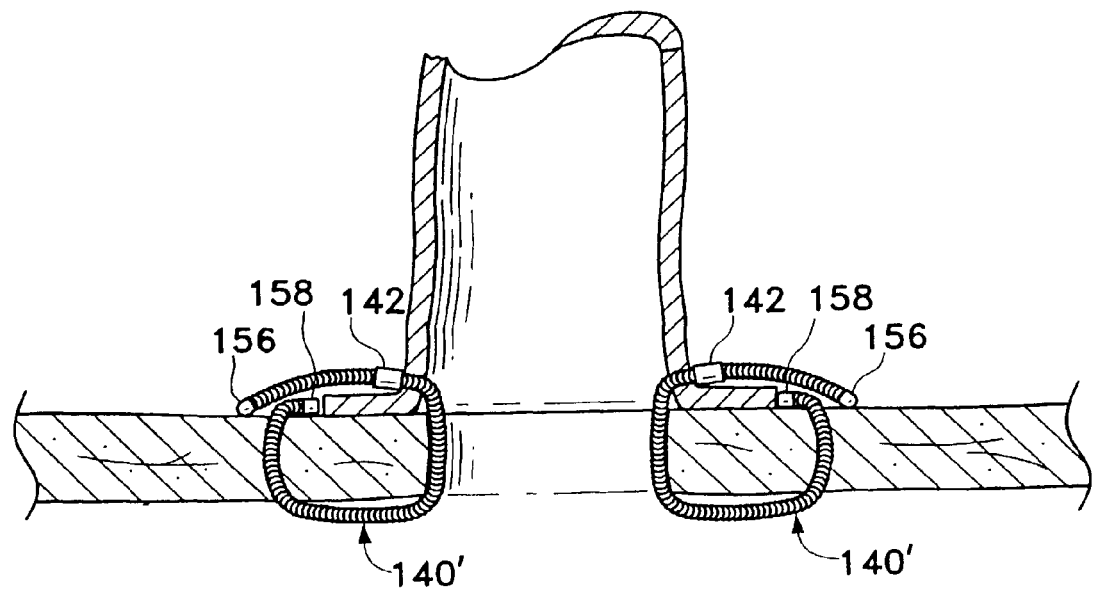

Referring to FIGS. 1B and 1C, a fastener 140' with two extensions and a stopper 142 is shown. The stopper preferably is slidably mounted onto the wire 154 in the vicinity of the transition from a curved wire portion, to the relatively straight extension. The stopper is placed between discrete springs 146" and 146''' and held in place thereby. Either or both of springs 146" and 146''' may be single or double coils (or more) as described above and may be set according to the procedures described with regard to coils 146 and 146'.

The embodiment of FIGS. 1B and 1C is particularly advantageous for anastamosing a relatively thin-walled vessel to a relatively thick-walled vessel (e.g., the aorta or other large vessel), where an extension acts to prevent the relatively thin-walled vessel from sliding into the anastomosis site and out of the preferred position where it is to be fixed, as is illustrated in FIG. 1C.

For example, this fastener design may be embodied by a wire (wire 154) having a cross-sectional thickness of about 0.0045 inches, which, in the closed configuration shown forms an inner loop having a diameter $D_1$ of about 0.060 inches and an outer loop dimension $D_2$ of about 0.065 inches. In the open configuration, the fastener forms a U-shape with a depth of the U-shape being about 0.07-0.09 inch (1.5 to 2 mm).

It is to be understood that the fasteners may have undeformed or deformed configurations different than those shown herein without departing from the scope of the invention. In addition, a locking clip (not shown) may also be attached to connect the ends of the fastener when the fastener is in its closed position to prevent possible opening of the fastener over time. The locking clip may also be integrally formed with one end of the fastener.

Figure 9:
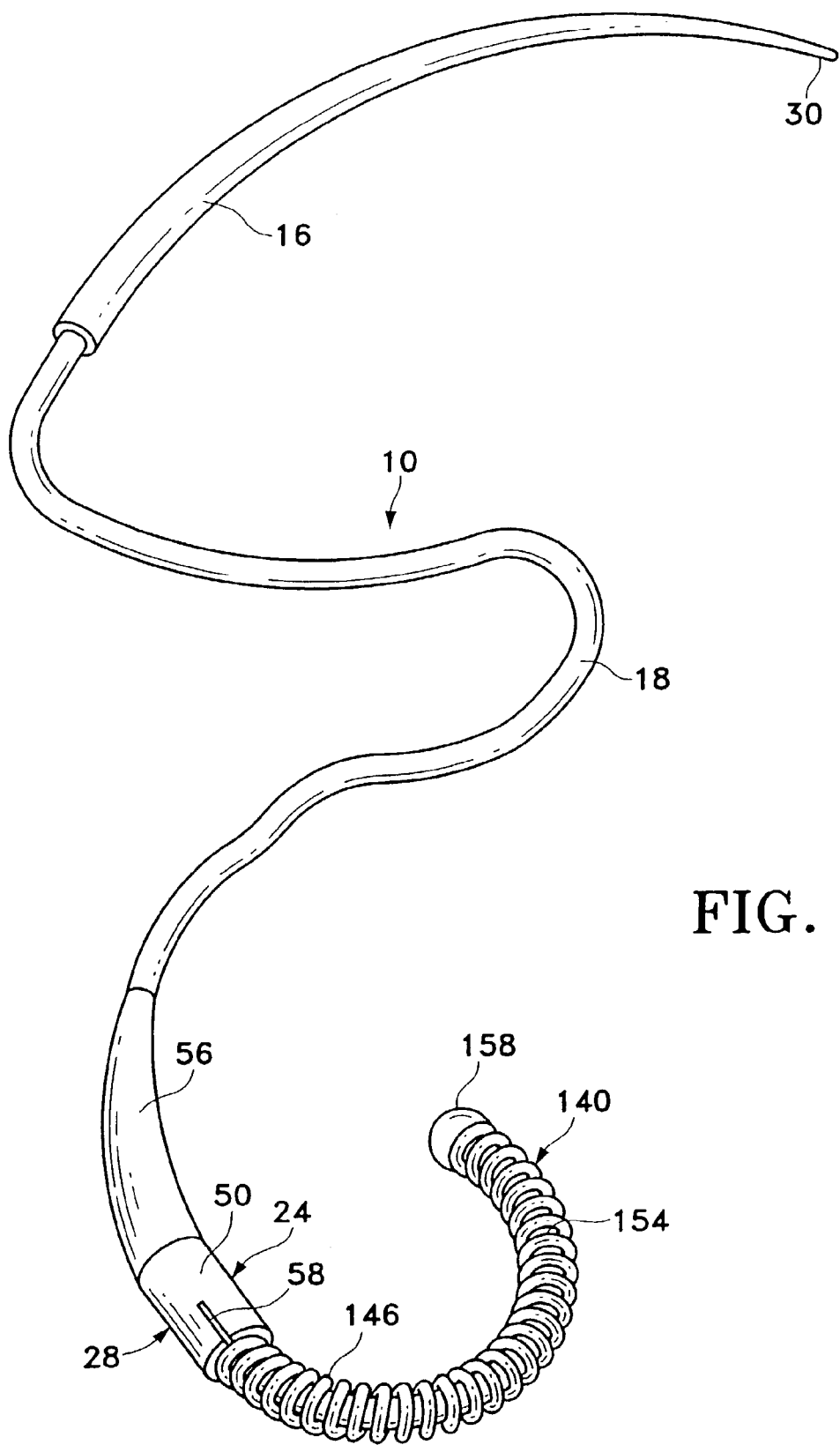
FIG. 9 is a tissue connector assembly, which may include the fastener of any of FIGS. 1-8.

In the example shown in FIG. 9, the tissue connector assembly 10 generally comprises a tissue piercing or penetrating member 16, a flexible member 18, and a fastener or surgical clip 140. A restraining device, generally indicated at 24 and comprising a spring (or coil) 146 and a locking device (or release mechanism or coupling member) generally indicated at 28, is connected to the fastener 140 for holding the fastener in a deformed configuration as further described below.

Piercing or penetrating member 16, which may be in the form of a needle (such as a 7-0 or 8-0 needle), has a sharp pointed tip 30 at its distal end for penetrating tissue. Member 16 may be bent as shown in FIG. 9, for example. The diameter of at least a portion of member or needle 16 is preferably greater than the diameter of flexible member 18 so that the flexible member can easily be pulled through an opening formed in the tissue by the needle. The distal end of member or needle 16 is preferably rigid to facilitate penetration of tissue. The remaining length of member or needle 16 may be rigid or flexible to facilitate movement of the needle through the tissue as further described below. The tip 30 of member or needle 16 may have various configurations and may, for example, be conical, tapered, or grounded to attain a three or four facet tip. Member or needle 16 may be made from stainless steel or any other suitable material, such as a polymeric material. It is to be understood that member or needle 16 may have a shape or radius of curvature other than the one shown, without departing from the scope of the invention. Member or needle 16 may also be integrally formed with the flexible member 18 (e.g., both needle and flexible member formed of the same material.)

Flexible member 18 may be in the form of a suture formed from conventional filament material, metal alloy such as Nitinol, polymeric material, or any other suitable material. The material may be non-stretchable or stretchable, solid or hollow, and have various cross-sectional diameters. The flexible member or suture may have a cross-sectional diameter of 0.003 inch, for example. The diameter and length of the suture will vary depending on the specific application. The suture may be attached to the needle 16 by crimping or swaging the piercing member or needle onto the suture, gluing the suture to the piercing member or needle, or any other suitable attachment method. Flexible member 18 may have cross-sectional shapes other than the one shown herein and may have other constructions as well.

Referring to FIGS. 10A and 10B, one release mechanism for coupling the fastener to the suture and needle is generally indicated with reference numeral 28a. Locking device or release mechanism 28a comprises a plurality of substantially rigid strands, preferably wires 106, arranged substantially parallel to one another and circularly about a longitudinal axis of the aligned strands, to form a tube-like configuration, as can be seen in the cross-sectional view of FIG. 10B. Alternatively, strands 106 may be cables or some other substantially rigid strand elements arranged in the same manner as the wires shown in FIG. 10B. Upon arrangement into the circular configuration, the hidden end portions 106a of the strands are coupled to tapered section 2, which is coupled to a piercing member or needle through a flexible member such as flexible member 18.

Preferably, a rod 162 extends from tapered section 2 to facilitate fixation of the strands thereto. The coupling of the strands to tapered section 2 is preferably accomplished by gluing or soldering to rod 162, although other equivalent or similar known joining techniques may be employed (e.g., welding, threadably attaching, etc). Similarly, rod 162 is preferably glued, soldered or threaded into the needle or transition element. In an alternate arrangement, the flexible member may extend through tapered section 2 and form a substitute structure for rod 162. This may be preferred when the flexible member is a metal wire.

The end portions 106b of the strands in the vicinity of the fastener strands include notches 109 which are formed into the strands to a depth equal to approximately half the diameter of the strand 106. When the strands are arranged in the circular configuration described above, the notches 109 form a chamber 108 configured for receiving and holding enlarged portion 156. Although enlarged portion 156 is shown as having a spherical shape, it may have other shapes including a barrel shape, or other shape that may be easily grasped and easily released.

The notches are preferably placed about 0.015" from the free ends of the strands, but this distance, of course, can be modified, depending upon the amount of compression of spring 146 that is desired when ball 156 is inserted into the chamber 108 and held by notches 109.

After placement of ball 156 within chamber 108 formed by notches 109, a shrink wrap layer, preferably a shrink tubing 110 may be provided over at least free end portions 106b of wires or strands 106, and the tubing heated to compress against strands 106 and hold them in place against ball 156, preferably symmetrically against ball 156. Together, tubing 110 and strands 106 effectively hold ball 156 captive within notches 109. Alternatively, other plastic or elastic restraining members may be mounted around the distal portions of the wires or strands to aid in maintaining them in place, preferably symmetrically against ball 156. Still further, strand members may be designed with an elastic spring force sufficient to maintain notches 109 in place with sufficient force to maintain the ball 156 captive therein under the tensile forces normally experienced during a suturing procedure. Although a seven strand embodiment is shown, it should be understood that fewer or more than seven strands may be used. The number of strands may vary depending on, for example, the size of the clip or the size of the strands. Typically, the number of strands may range from two to ten. In a coronary anastomosis, the number of strands preferably will range from five to seven although other numbers may be used.

In assembly, enlarged portion 156 of wire 154 is placed in chamber 108. Tubing 110 is wrapped around at least a portion of the strands (as shown in the drawings) and heated to maintain enlarged portion 156 captive within the cavity formed by the strands. Compression coil or spring 146 is slid over wire 154 and enlarged portion 158 is slid over the wire 154 and slid against spring 146 to compress the coil against portions 106b such that the fastener is in its open configuration. Enlarged portion 158 may then be swedged or otherwise fixed to wire 154 to maintain the fastener in its open configuration.

Release mechanism 28a is movable between a locked position and an unlocked position. In the locked position the ball 156 is held within notches 109 and consequently, coil 146 is held in its compressed position, thereby maintaining fastener wire 154 in its deformed or open position. In the unlocked position, ball 156 is released from the notches, thereby allowing the coil 146 to expand, and releasing the closing forces produced by both the wire 154 and the coil 146, causing the fastener 140 to close. As noted above, the coil 146 remains integral with the wire 154 upon closing of the fastener 140. The closing actions or forces provided by the wire 154 and coil 146 act in concert to provide an optimal closing force of the fastener upon the tissues, tissue and graft, etc. The coil 146 remains integral with the wire or clip 154 after closing of the fastener 140, and both components cooperate to maintain the anastomosis.

Movement of the release mechanism to the open position is accomplished by applying a compressive force to the shrink tube 110 and bundle of strands 106. Advantageously, the compressive force may be applied at any opposing locations around the circumference of the shrink tube as long as the implement applying the force is oriented at an angle to the strands, preferably substantially perpendicular thereto, to allow the implement to traverse the strands so as to deform the positions thereof when the force is applied. The strands or wires 106 get distorted from their circular configuration under the compression. This change in shape stretches the shrink tube 110 from a circular configuration to a somewhat elliptical configuration, and removes some of the notches 109 from contact with ball 156, thereby permitting removal of ball 156 from within the chamber previously formed by notches 109 in the closed position.

Figure 11A:
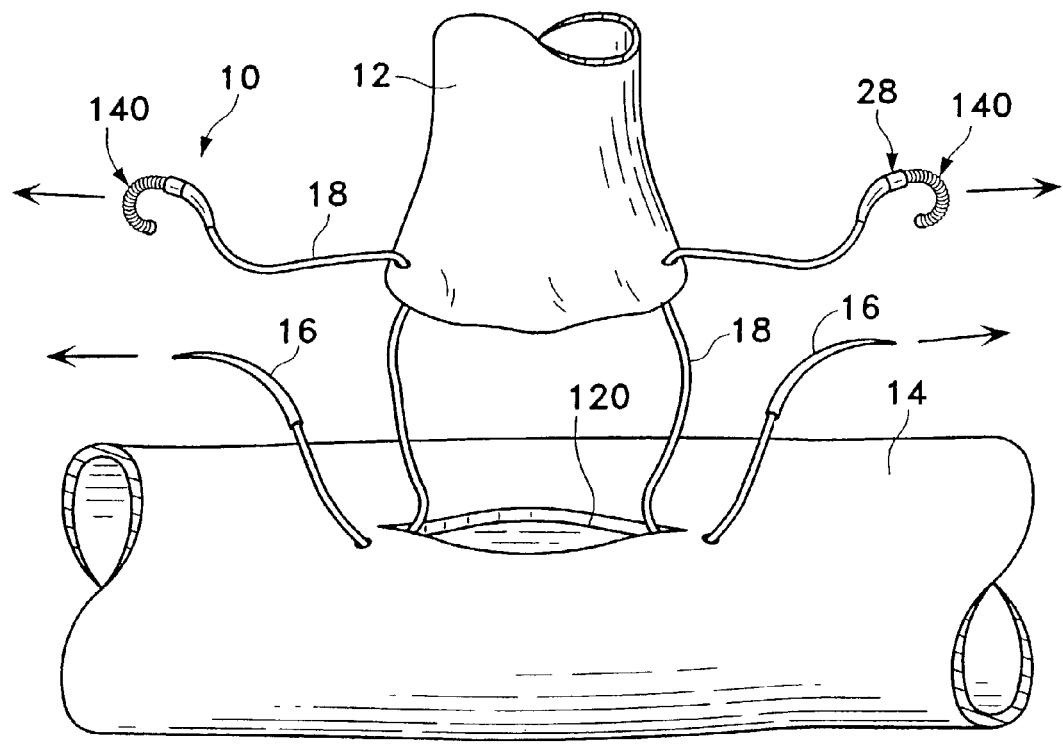
FIGS. 11A, 11B and 11C diagrammatically illustrate the placement of fasteners in an anastomosis.
Figure 11B:
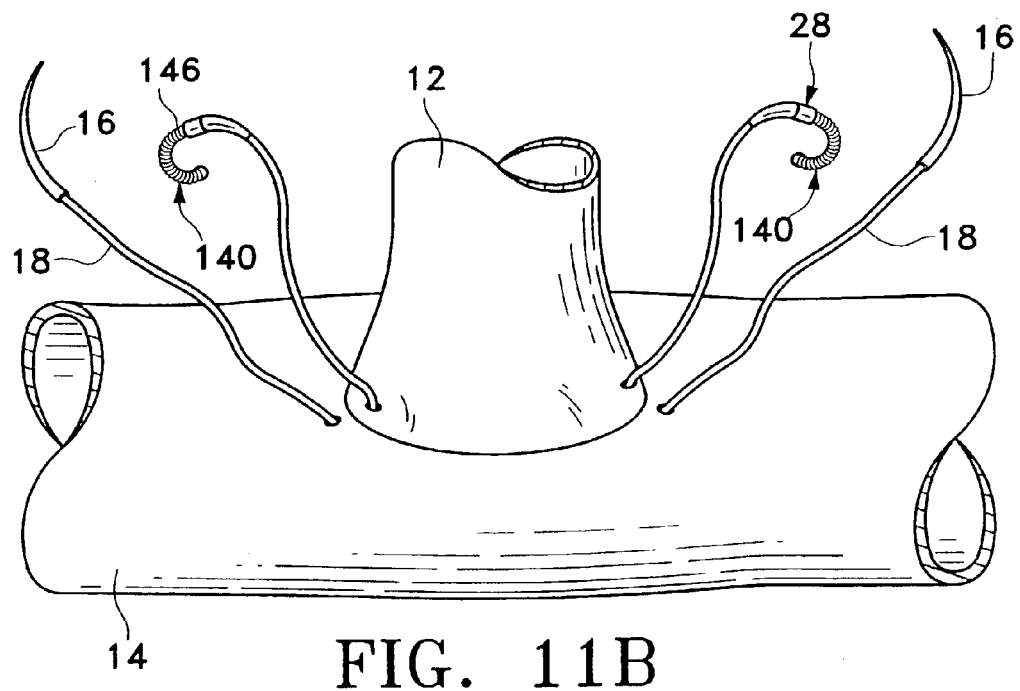
Figure 11C:
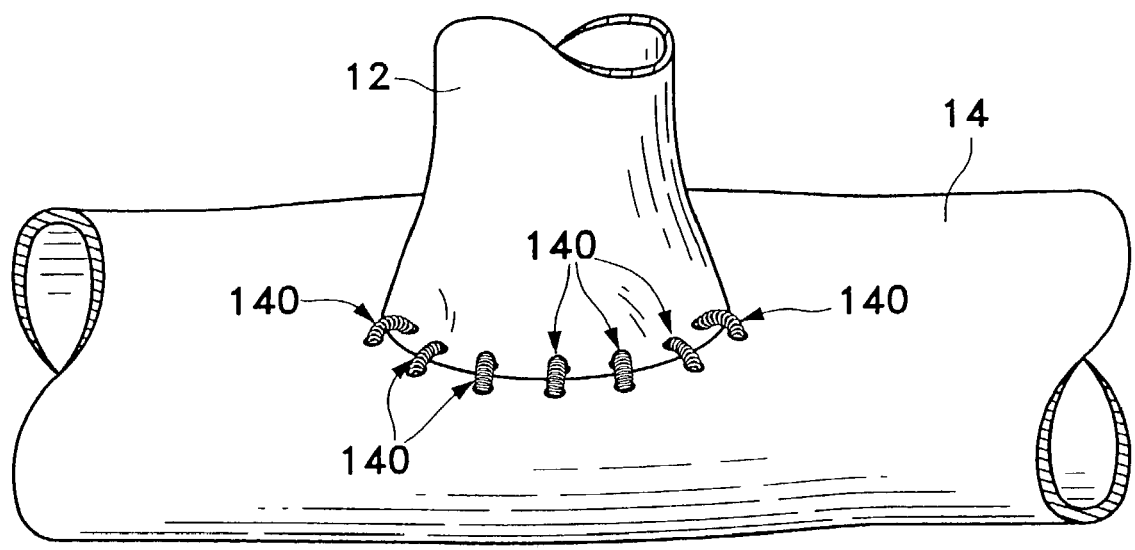

The tissue connector assembly 10, has many uses. It may be especially useful for minimally invasive surgical procedures including creating an anastomosis between a vascular graft 12 and an artery 14 (FIGS. 11A-11C). The anastomosis may be used to replace or bypass a diseased, occluded or injured artery. A coronary bypass graft procedure requires that a source of arterial blood flow be prepared for subsequent bypass connection to a diseased artery. An arterial graft may be used to provide a source of blood flow, or a free graft may be used and connected at the proximal end to a source of blood flow. Preferably, the source of blood flow is one of any number of existing arteries which may be dissected in preparation for the bypass graft procedure. In many instances it is preferred to use the left internal mammary artery (LIMA) or the right internal mammary artery (RIMA), for example. Other vessels which may be used include the saphenous vein, gastroepiploic artery in the abdomen, radial artery, and other arteries harvested from the patient's body as well as synthetic graft materials, such as DACRON® (polyester fibers) or GORETEX® (expanded polytetrafluoroethylene). If a free graft vessel is used, the upstream end of the dissected vessel, which is the arterial blood source, will be secured to the aorta to provide the desired bypass blood flow, as is well known by those skilled in the art. The downstream end of the graft vessel is trimmed for attachment to an artery, such as the left anterior descending coronary (LAD). It is to be understood that the anastomosis may be formed in other vessels or tissue.

The patient is first prepped for standard cardiac surgery. After exposure and control of the artery 14, occlusion and reperfusion may be performed as required. An arteriotomy is performed on artery 14 to provide an opening 120 for receiving a graft vessel (FIG. 11A). After the snared graft vessel 12 has been prepared and made to the appropriate length as would be conventional in the art, a tissue connector assembly 10 is attached to the free end of the graft vessel along an edge margin of the vessel. In order to attach the connector assembly 10, the surgeon grasps the needle 16 with a needle holder (e.g., surgical pliers, forceps, or any other suitable instrument) and inserts the needle 16 into the tissue of the graft vessel 12 in a direction from the exterior of the vessel to the interior of the vessel. The surgeon then releases the needle 16 and grasps a forward end of the needle which is now located inside the graft vessel 12 and pulls the needle and a portion of the suture 18 through the vessel. The needle 16 is passed through opening 120 formed in the sidewall of the artery 14 and inserted into the tissue of the artery in a direction from the interior of the artery to the exterior of the artery. The surgeon then grasps the needle 16 located outside the artery 14 and pulls the needle and a portion of the suture 18 through the arterial wall. A second tissue connector assembly 10 may be inserted at a location generally 180 degrees from the location of the first tissue connector in a conventional "heel and toe" arrangement.

Once the tissue connector assemblies 10 are inserted, the graft vessel 12 is positioned above and aligned with the opening 120 in the sidewall of the artery 14 (FIG. 11A). A section of each suture 18 is located between the graft vessel 12 and artery 14. The fasteners 140 and needles 16 are pulled generally away from the artery 14 to reduce the length of the suture 18 (eliminate slack of the suture) between the vessel 12 and artery and "parachute" the vessel onto the artery (FIG. 11B). The needles 16 are then pulled away from the artery 14 until each fastener 140 is positioned within the graft vessel 12 and artery with one end of each fastener 140 extending from the vessel and the opposite end of each fastener extending from the artery.

A surgical instrument (e.g., needle holder) is used to radially squeeze each locking device 28 to release the locking device from the fastener 140. Upon removal of the locking device 28, the coil 146 moves to its free uncompressed state which allows both the wire 154 and coil 146 to return to their memory configurations which define the closed position (FIG. 11C). As the wires 140 move to their closed positions the adjacent tissues of the graft vessel 12 and artery 14 which were previously pulled together during the parachuting of the graft vessel onto the artery, are squeezed together to securely engage the graft vessel and artery. The graft and arteriotomy edges may be abutted or everted as is known in the art. It should be noted that as the locking device 28 is squeezed two steps are accomplished. The fastener 140 is released from the locking device 28, thus allowing the coil 146 to uncompress and the wire 154 and coil 146 to close, and the needle 16 is released from the fastener. Thus, in this embodiment, the locking device 28 provides for simultaneous actuating closure of the fastener 140 and release of the needle 16 from the fastener.

In this example, two tissue connector assemblies 10 are used to make connections at generally opposite sides of the graft vessel. Additional tissue connector assemblies 10 may be used to make connections between those. The procedure may be accomplished with a beating heart procedure with the use of a heart stabilizer to keep the heart stable, for example. The procedure may also be performed endoscopically.

As an alternative to inserting tissue connector assemblies 10 at "heel and toe" locations described above, a number of tissue connectors 10 may be inserted generally around the location of the heel. The graft vessel may then be pulled towards the artery to determine whether the opening formed in the sidewall of the artery is large enough before completing the anastomosis. In a further alternative, double needle assemblies 11 (FIG. 12 described below) are used. Each needle of a double needle assembly 11 is passed from inside to outside of the respective graft and artery. The first assembly is placed at the "heel" (6 O'clock) position, the tissue brought together in the clip and the clip closed. Another double needle assembly is then placed a the 5 O'clock position and closed, 7 O'clock position and closed, 12 O'clock position and closed, 1 O'clock position and closed, 11 O'clock position and closed. Three single needle assemblies 10 are then evenly spaced between the 6 and 12 O'clock positions (placed laterally) and the tissue placed therein. These fasteners are then closed. Three more single needle assemblies 10 are placed on the other lateral side of the anastomosis in the same manner as the first lateral fasteners.

Figure 12:
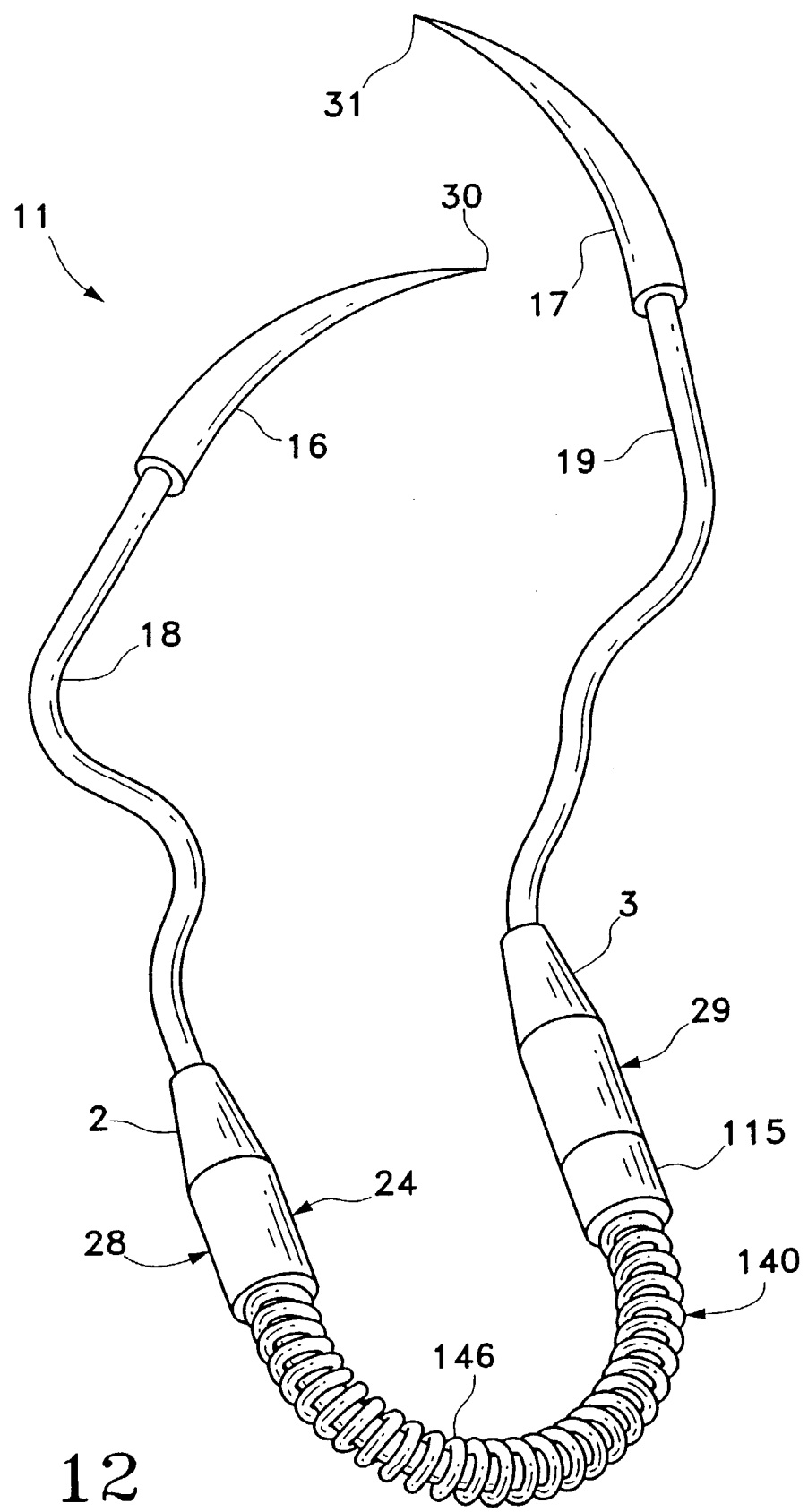
FIG. 12 shows a double needle tissue connector assembly.

Referring to FIG. 12, the multiple piercing member construction facilitates threading ends of the assembly from inner to outer wall(s) of material, such as tissue, which may eliminate or minimize the possibility of dislodging material, such as plaque, from the inner wall of calcified arteries, for example, as will become more apparent from the description provided below. In a preferred embodiment, two piercing members, each of which may comprise a needle, are releasably coupled to a fastener. The coupling between the flexible member (and, thus, the piercing member) and the fastener may be constructed to actuate closure of the fastener upon release of the flexible member (or piercing member). For example, the coupling may hold a compression spring (which is positioned around a fastener) in a compressed state to brace the fastener open and releasably lock or secure the fastener to the flexible member (or piercing member).

As shown in FIG. 12, a tissue connector assembly 11, which generally comprises tissue piercing or penetrating members 16 and 17, flexible members 18 and 19, and a fastener 140 (e.g., a surgical clip) is shown. A restraining device, generally indicated at 24 and comprising a spring (or coil) 26 and a locking device (or coupling member) generally indicated at 28, is connected to fastener 140 for holding the fastener in a deformed or open configuration as described previously. That is, the spring or coil is adapted to be integrated with the wire or clip, to act in concert therewith, for closing the fastener with and optimal closing force and action. Penetrating or piercing member 17 may be made in accordance with the description provided above in connection with penetrating member 16, and, thus may, for example, be in the form of a needle (such as a 7-0 or 8-0 needle) having a sharp pointed tip 31 at its distal end for penetrating tissue. Members 16 and 17 may be the same or differ from one another. Flexible members 18 and 19 also may have the same construction.

Referring to FIG. 13A, release mechanism 28*a* also may be used to releasably couple the other end of the fastener to another flexible member such as flexible member 19, which in turn, is coupled to a needle such as needle 17 as shown in FIG. 12. In this arrangement, a member or stopper 115, which may be annular, is secured to the other end of the fastener or wire 154 to prevent enlarged portion 156 or 158 (since wire 154 may have substantially symmetrical ends when employing double penetrating members) from passing through the compression spring upon release from release mechanism 28*a*.

FIGS. 13B and 13C illustrate a synchronized fastener release system. One release mechanism may correspond to mechanism 28*a*. At the other end of the fastener or wire 154, a release mechanism which responds to the compressive state of coil 146 and releases the fastener or wire 154 upon release of compressive forces on the coil is shown and generally designated with reference numeral 29*a*. Referring to FIGS. 13B and 13C, release mechanism 29*a* comprises two members 121 each having a recess 122 formed therein and arranged to form chamber 124 when members 121 are aligned as shown in FIG. 13B. Recesses 122 are configured to retain enlarged portion 156 or 158, which is shown with a cylindrical configuration, but may have a spherical or other suitable shape for operatively associating with a suitably configured chamber. Further, members 121 may have semicircular transverse cross sections or some other combination of transverse shapes that can collectively provide the desired chamber to retain enlarged portion 156 or 158. The number of members 121 also may vary as would be apparent to one of ordinary skill.

Release mechanism members 121 have tapered ends 126, which are configured for positioning between coil 146 and fastener wire 154 as shown in FIG. 13B. When tapered ends 126 are so positioned and coil 146 is in a compressed state, coil 146 holds tapered ends 126, which are normally biased away from each other, sufficiently together to retain enlarged portion 156 or 158 within chamber 124. When release mechanism 28*a* is actuated (e.g., radially compressed) to release enlarged portion 156 or 158 of fastener wire 154, coil 146 assumes its relaxed state, thereby releasing tapered ends 126 of release mechanism 29*a* from the coil and allowing the tapered ends to radially expand and release enlarged portion 156 or 158 of fastener wire 154. Accordingly, both needles and flexible members may be decoupled from the fastener when release mechanism 28*a* is actuated.

FIGS. 14A-14C show another synchronized fastener system which is similar to the system shown in FIGS. 13A-13C. Release mechanism 28*c* may be of the type described above with regard to reference numeral 28*a* or may be a variety of other mechanisms including those described in copending, commonly assigned application Ser. No. 09/090,305, filed Jun. 3, 1998; Ser. No. 09/089,884, filed Jun. 3, 1998; Ser. No. 09/259,705, filed Mar. 1, 1999; and Ser. No. 09/260,623, filed Mar. 1, 1999; all of which are incorporated herein by reference thereto, in their entireties. Release mechanism 29*b* and the cooperating portion of the fastener or wire 154 are also varied from release mechanism 29*a*. In this embodiment, an annular member or stopper 115, which may be annular, is slidably coupled to fastener wire 154. Member 115 is configured to resist passage of coil 146 thereover. Accordingly, member 115 may have an outer diameter slightly greater than at least the portion of the coil adjacent thereto. A tapered or frustoconical member 3' is secured to an end of fastener wire 154, which need not include an enlarged portion. Member 3' is the same as member 3 with the exception that member 3' has a channel 134 for receiving flexible member or suture 19. Channel 134 extends radially outward from bore 132, which is formed through member 3', for receiving the fastener or wire 154 (FIG. 14C).

Flexible member 19 is threaded through channel 134 and between tapered member 3' and annular member 115. When coil 146 is in a compressed state as shown in FIG. 14A, the coil urges member 115 toward tapered member 3' and compresses flexible member 19 therebetween. In this manner, flexible member 19 is secured to the fastener or wire 154. When release mechanism 28*c* is actuated (e.g., radially compressed) to release enlarged portion 156 of the fastener or wire 154, coil 146 assumes its relaxed state so that annular member 115 may slide away from tapered member 3' and release flexible member 19. Accordingly, both needles and flexible members may be removed from the fastener when release mechanism 28*c* is actuated. Although a metal flexible member may be used, a polymeric flexible member may be preferred.

Because of its potentially very small size and its tendency to wrap itself snugly around tissue, the fastener may not leave much to grab onto for its removal if desired. In addition, there may be no free ends to grab, which may make it difficult to remove without damaging the tissue around which it is wrapped. The following is a detailed description of removal apparatus and methods according to the present invention.

Figure 15A:
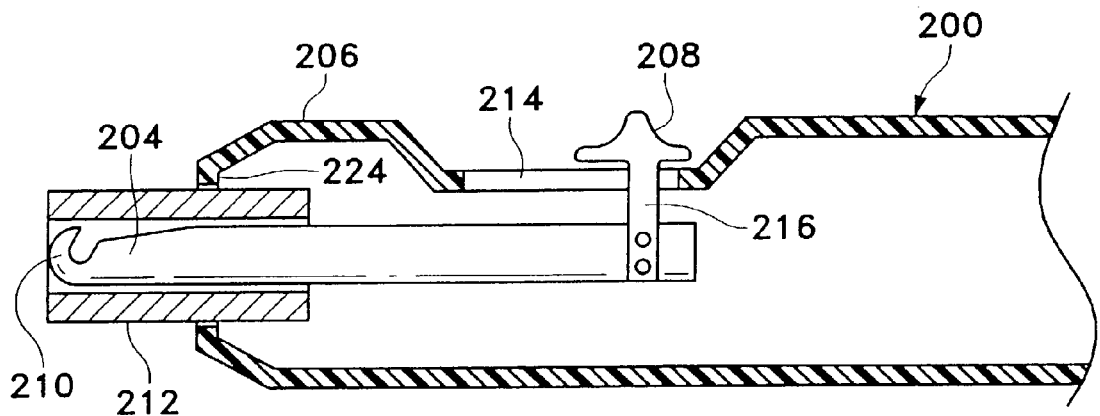
FIGS. 15A, 15B and 15C show fastener removal apparatus which may be used with the present invention where
Figure 15B:
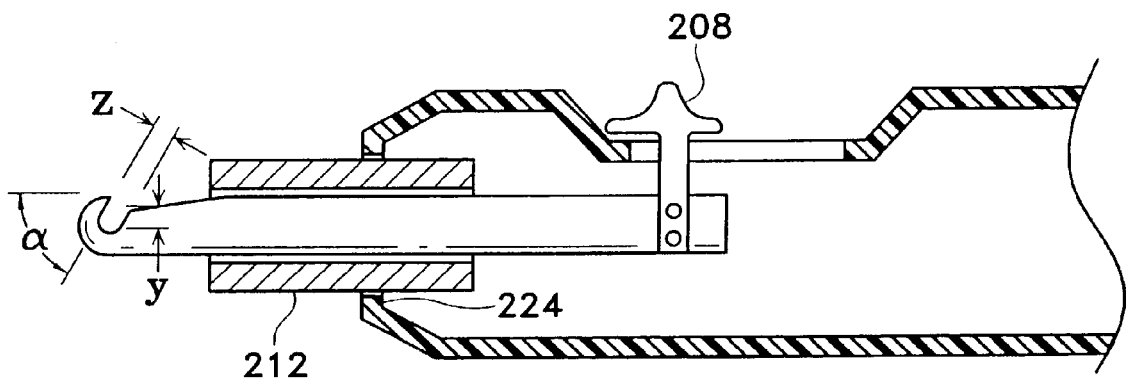
Figure 15C:
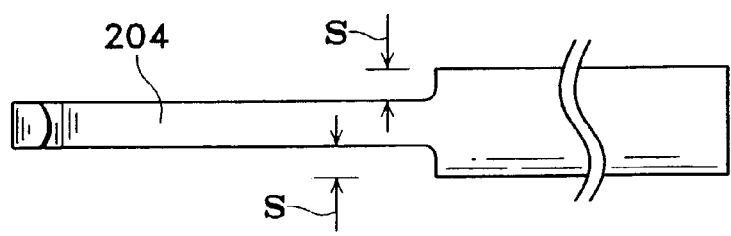
Figure 16A:
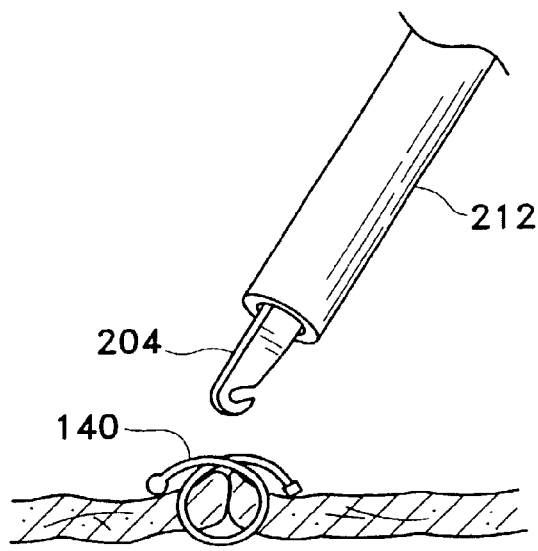
FIGS. 16A, 16B, 16C and 16D diagrammatically illustrate removal of a fastener with the apparatus of FIGS. 15A-C.
Figure 16B:
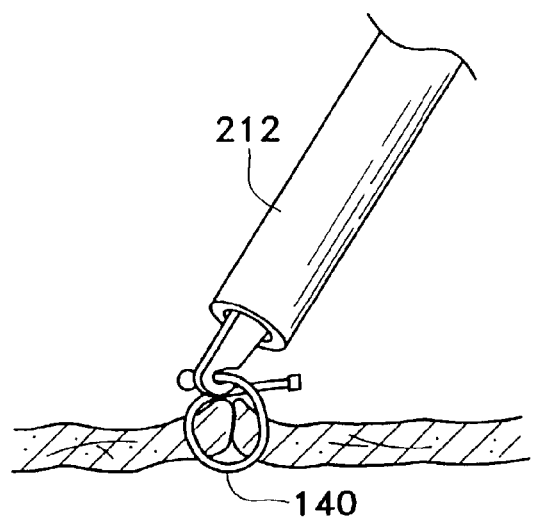
Figure 16C:
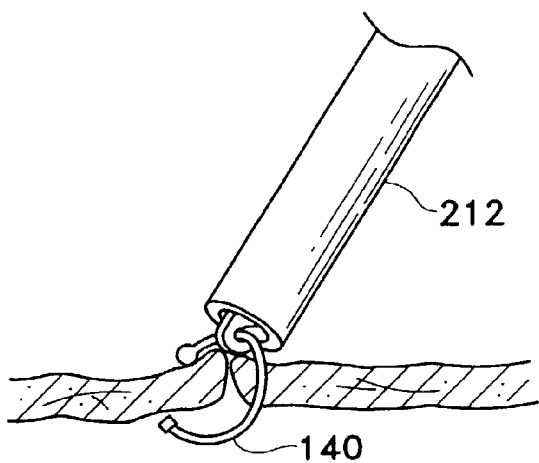
Figure 16D:
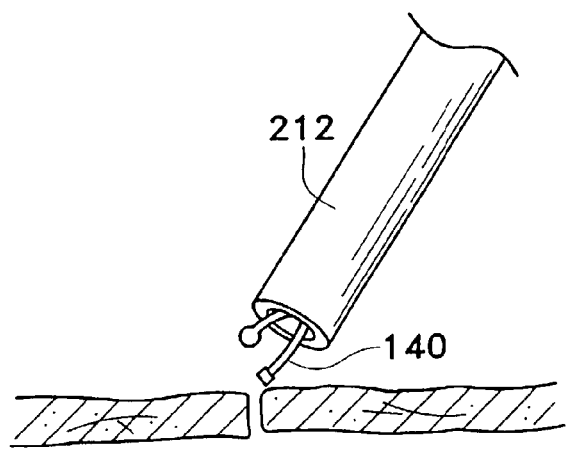

Referring to FIGS. 15A-15C, one embodiment of a removal apparatus 200 is shown. In the embodiment, the apparatus generally comprises a grabber member 204 having a hook 210 and slidably mounted within sleeve 212. Sleeve 212 may have a blunt distal end so that it may restrain tissue movement as the fastener is drawn therefrom. Sleeve 212 may be mounted within housing 206, which includes a slot 214 through which flange 216 of sliding button 208 is disposed. One end of the flange 26 is secured to the grabber member so that the grabber member can be withdrawn and extended from the sleeve as shown in FIGS. 15A and 15B.

The hook may be formed at an angle of about 50-70 degrees (α) and has a width ("z") and depth ("y") slightly larger than the diameter of wire 154 and coil 146 (or 146', 146", 146'") (e.g., about 0.001 inch greater than the diameter of the wire and coil). "z" and "y" thus may be essentially the same and may be in the range of about 0.005-0.020 inch. This configuration has been found to enhance the grabber member's ability to grab the fastener and pull it out of the tissue or material in which it is placed.

Referring to FIGS. 16A-16D, fastener removal is diagrammatically shown. After the fastener wire is placed in the slot of the hook, it is pulled inside the tubular sleeve 212. As the fastener enters the sleeve, it is bent in half and the coils surrounding the clip wire are compressed down towards the ends of the clip. This bending of the clip wire, combined with the compression of the coil causes the clip to open up enough to be pulled out of the tissue without damaging it and up into the tube or sleeve 212. As shown in FIG. 15C, which is a top view of the grabber member, a portion of the grabber member adjacent the hook, has a reduced thickness to provide sufficient space for the fastener to be drawn within the sleeve, while straightening the wire and coil as it is pulled therein. The space "s" on each side of the member generally corresponds to the diameter of the wire and coil and may range, for example, from about 0.004 to 0.010 inch.

The hooked grabbing member can be retracted into the tube as described above. Alternatively, the sleeve 212 can be slidably mounted in housing 206 and attached to flange 216 of button 208, with the hooked grabbing member being fixed to the housing 206. In this variation, one can slide button 208 along slot 214 to slide sleeve 212 over the grabbing member to open or straighten the fastener.

Although a hooked grabbing mechanism is shown, it should be understood that other grabbing mechanisms can be used. Examples of other mechanisms include, but are not limited to, alligator-type jaws or a lasso-like wire loop as shown in FIGS. 17A-B and 18A-B, respectively. In the jaws variation, the jaw portion has a reduced width to allow entry of the fastener as in the hooked grabber as shown in FIG. 15C. In the loop embodiment, the sleeve lumen is sufficiently small to generally straighten the fastener 140.

Figure 17A:
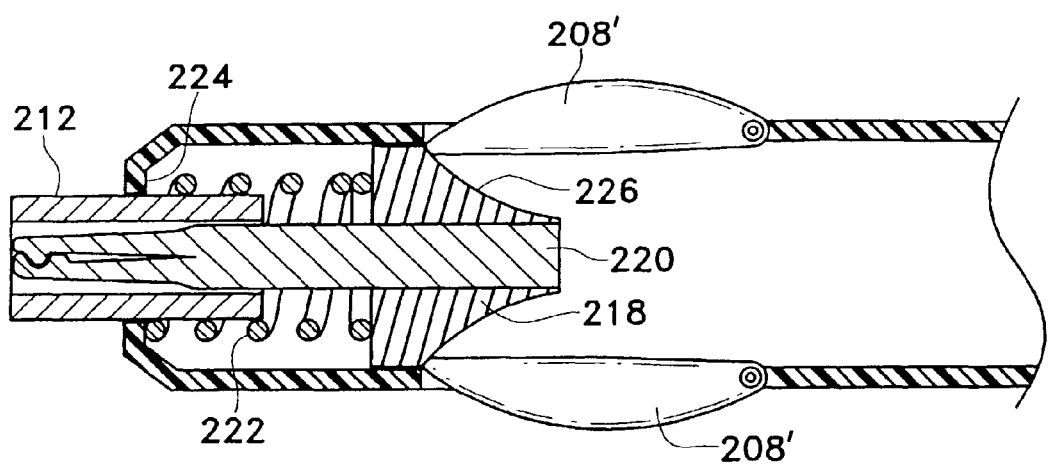
FIGS. 17A and 17B are sectional views of another embodiment of the fastener removal apparatus.
Figure 17B:
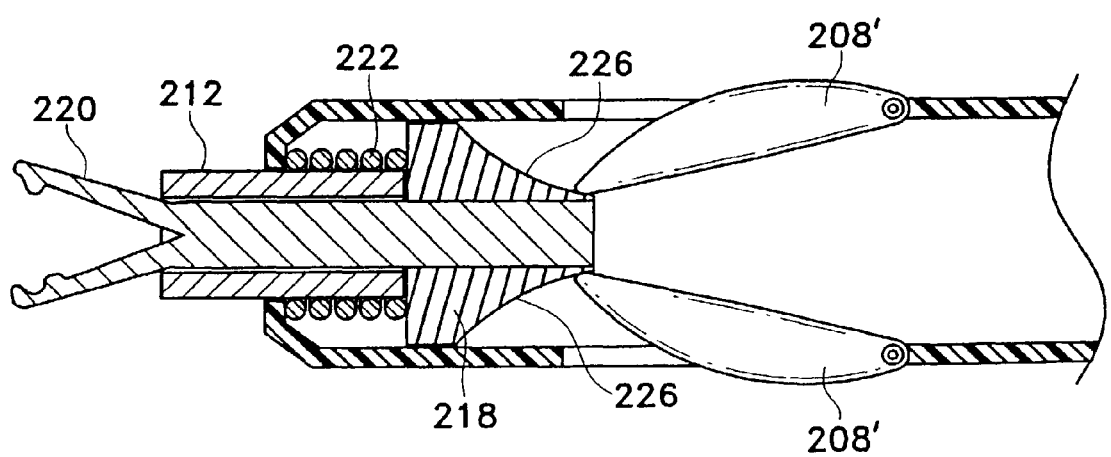

Another grabber displacement mechanism also is shown in FIGS. 17A and 17B for use with the present invention. According to this embodiment, a cam system is used to actuate movement of the grabber member. Although not shown, it should be understood that the cam system can be arranged to reciprocate the sleeve instead of the grabber member. One or more buttons 208' are pivotally mounted to housing 206 to engage cam member 218, which may be in the form of a frustoconical member surrounding a portion of the grabber member, such as jaws type grabber member 220. A restraint such as coil spring 222 is placed between the cam member and housing annular flange 224 to bias the grabber into the sleeve as shown in FIG. 17A. As the buttons 208' are squeezed, the buttons engage camming surfaces 226 and force the grabber member out from sleeve 212 as shown in FIG. 17B.

Figure 17C:
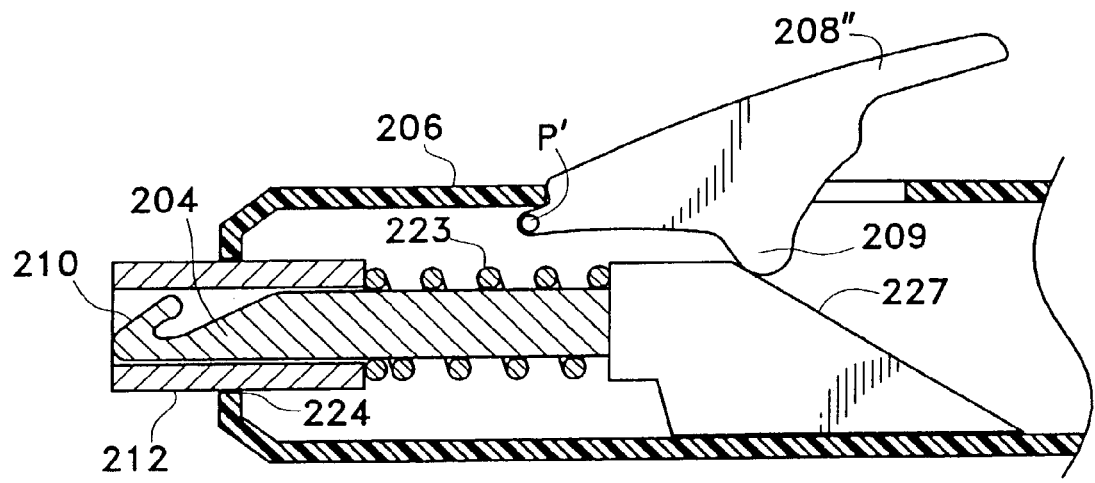
FIGS. 17C and 17D are sectional views of a variation of the cam mechanism of FIGS. 17A and 17B in combination with the hooked fastener grabber of FIGS. 15A-C.
Figure 17D:
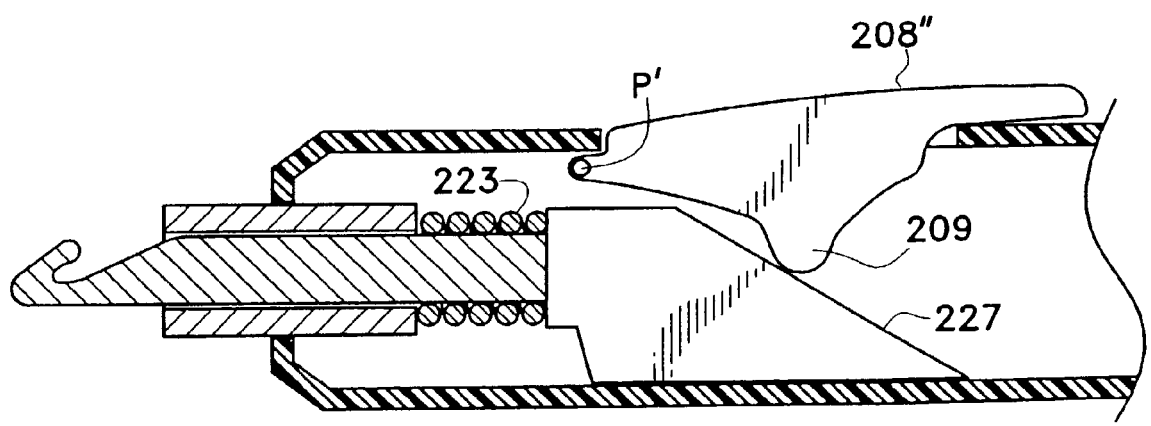

Further cam actuated grabber displacement mechanisms are shown in FIGS. 17C-D. These cam systems also are used to actuate movement of the grabber member. Actuator or cam member 208" is pivotally mounted to housing 206 at pin "p'". The actuator comprises a lever arm and camming projection or interface 209 which extends from the lever arm to engage camming surface 226' of cam follower member 218'. Cam follower 218' preferably is secured to one end of the grabber member, which may be hook grabber member 204. A restraint, such as coil spring 223, is placed between the cam follower and sleeve 212 to bias the grabber into the sleeve as shown in FIG. 17C. As the actuator 208" is squeezed, cam projection 209 moves along camming surface 226' and imparts translational motion to the cam follower, which in turn, forces the grabber member out from sleeve 212 as shown in FIG. 17D.

Although not shown, it should be understood that any of the cam systems shown in FIGS. 17A-D can be arranged to reciprocate the sleeve instead of the grabber member.

Figure 18A:
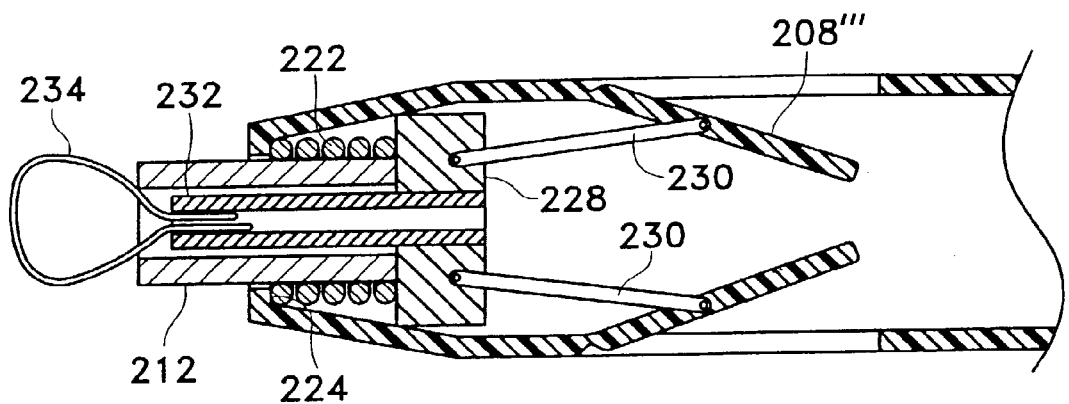
FIGS. 18A and 18B are sectional views of another embodiment of a fastener removal apparatus that may be used with the present invention.
Figure 18B:
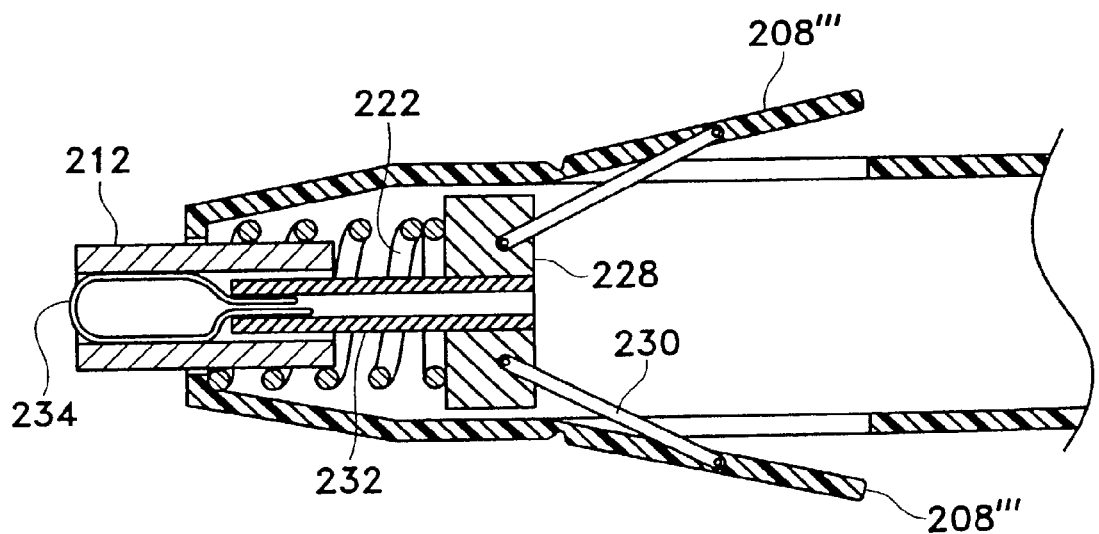

Referring to FIGS. 18A and 18B, another actuating mechanism is shown in combination with a loop grabber. Instead of a camming surface, a simple linkage mechanism can provide the downward force when the buttons are squeezed. These opposing buttons may be hinged to the handle, 180 degrees apart. The buttons may comprise flaps 208'" extending from the housing and pivotally movable relative thereto. As in the illustrated embodiment, a circumferential groove 228 can be formed in the housing at the juncture where the flaps extend to enhance the pivoting capability of the flaps. As the flaps are compressed with the thumb and forefinger, they axially drive piston 228 through arms 230. Each arm is pivotally coupled to a flap and the piston as shown in the drawings. The piston is biased against such axial movement through coil spring 222, which is mounted between the piston and annular flange 224 of the housing. The piston is secured to the elongated grabber member 232 (which has loop 234 extend therefrom) so that the grabber member travels or reciprocates with the piston. The number of buttons may vary. For example, a single button actuator design can be used. It also should be understood that any of the actuating mechanisms and grabber mechanisms described above may be combined.

Figure 19C:
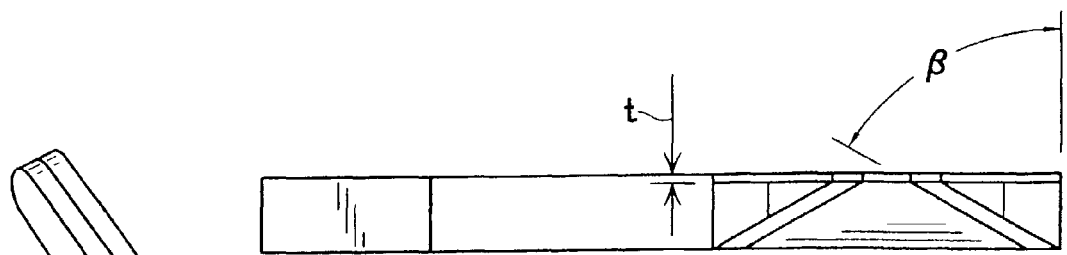
FIGS. 19A, 19B and 19C show another embodiment of a fastener removal apparatus that may be used with the present invention.
Figure 19A:
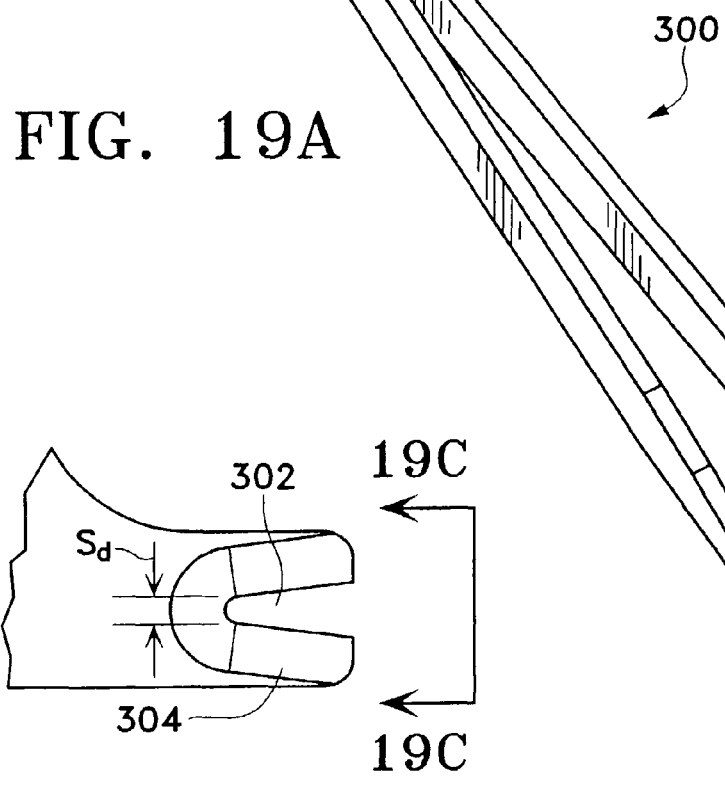
Figure 19B:
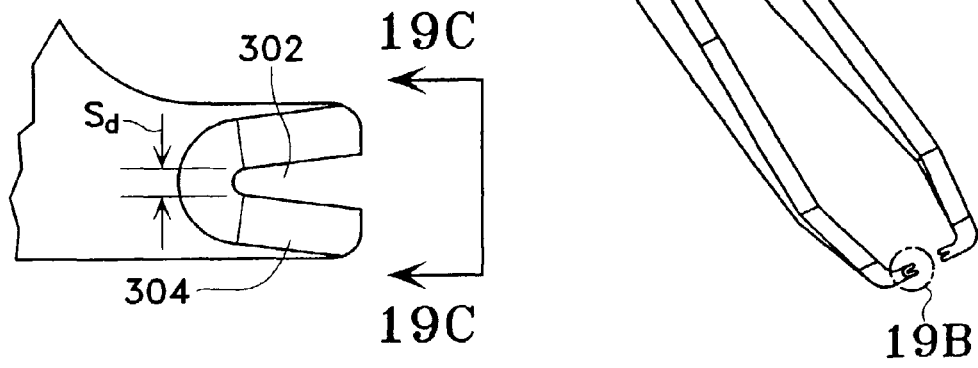
Figure 20A:
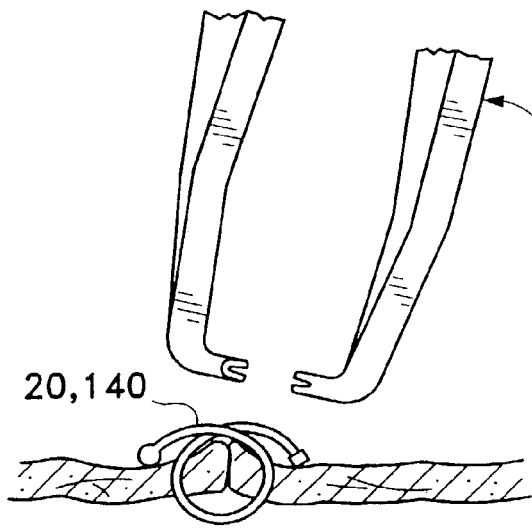
FIGS. 20A, 20B, 20C and 20D diagrammatically illustrate removal of a fastener using the apparatus of FIGS. 19A-C.
Figure 20B:
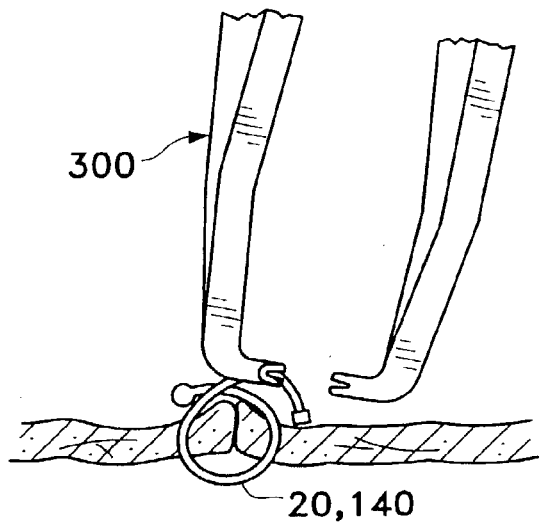
Figure 20C:
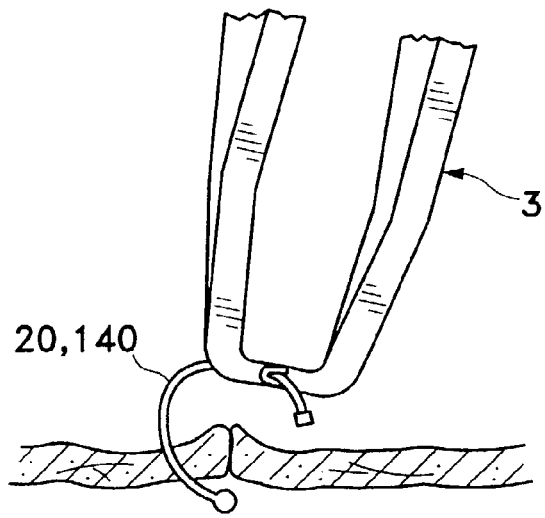
Figure 20D:
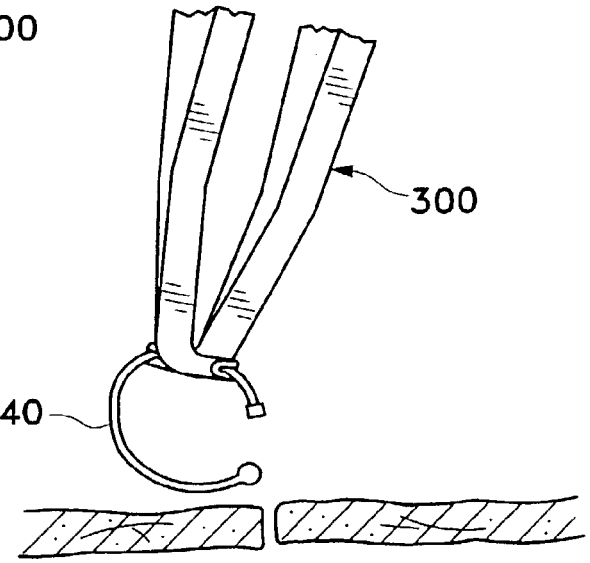

Referring to FIGS. 19A-19B, one embodiment is shown comprising a generally a two-part design that when assembled, resembles a pair of surgical tweezers or forceps. This embodiment is generally designated with reference numeral 300. There are two legs to the tweezers. The distal tip of each leg tapers down to less than about 0.010 inch thickness ("t", see FIG. 19C) at which point there is approximately a 90 degree bend inward, toward the other leg of the tweezers. This bent portion extends inward some distance (which may be about 0.1 inch) and may be about 0.035" in height. There is a slot cut through this bent-in portion that is the shape of a "V" or a "tapered U" and generally designated with reference numeral 302. The deepest part of the slot $S_d$ is equal to or slightly larger than the diameter of the fastener wire 154. The other end of the slot is greater than the combined diameter of the wire 154 and coil 146 (146',146",146'") of the fastener. As the fastener moves in toward the closed end of the slot, the beveled portions wedge between coil turns and compresses the coil. The beveled portions each comprise a chamfer which extends all around slot 302. This forms something resembling a two-tined fork. One side of this thin profile member is completely flat, while the other side is chamfered around the "V" profile (See FIG. 19C where 13 is about 55-65 degrees and may vary depending on the amount of taper to reach dimension "t"). The bevel is generally designated with numeral 304 (FIG. 19B). The flat sides of the member on each leg face each other, while the chamfered surfaces face outward away from each other. When the tweezers legs are squeezed together, the two flat, profiled, protruding members cross each other, with little or no space between their respective flat surfaces, somewhat resembling the shearing action of two scissors blades.

Referring to FIGS. 20A-20D, an example of fastener removal is shown. The surgeon simply brings one of the protruding members (forked parts) in at a right angle to the clip, and catches a portion of the clip in the "V" profile (between the tines of the fork). Once an arm of the clip is secured in the bottom of the "V", the tweezers legs are squeezed together. As the two protruding members are brought into proximity (one with the clip in it), the clip becomes engaged in the "V" groove of the second member. At this point the clip is resisting (trapped) between the bottoms of the two "V" grooves. As the tweezers are squeezed further, the edges of the two "V" grooves are forced between the coils of the clip and, thus, come into contact with the clip wire itself. As the tweezers are squeezed further, two things occur: (1) the coils surrounding the clip wire are pushed to the ends (compressed), which inherently causes the clip to begin to straighten, and (2) the wire begins to bend. The combination of these two things (as in each grabber member apparatus described above) causes the clip to open slightly and loosen its grip on the tissue. This allows the clip to be extracted from the tissue.

Figure 21:
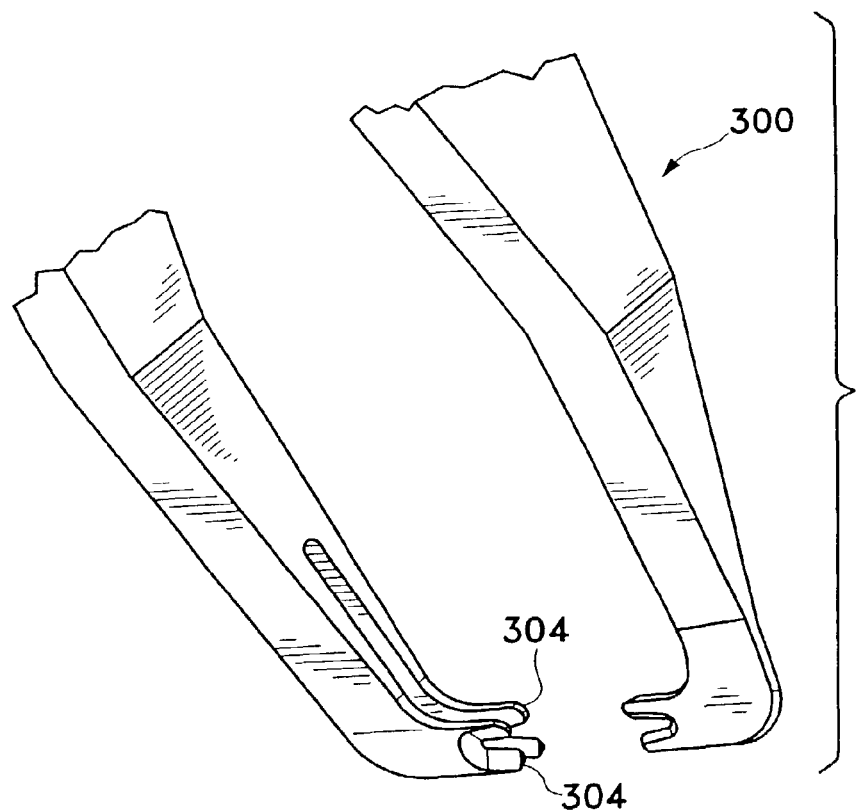
FIG. 21 shows a variation on the apparatus of FIGS. 19A-C.
Figure 22:
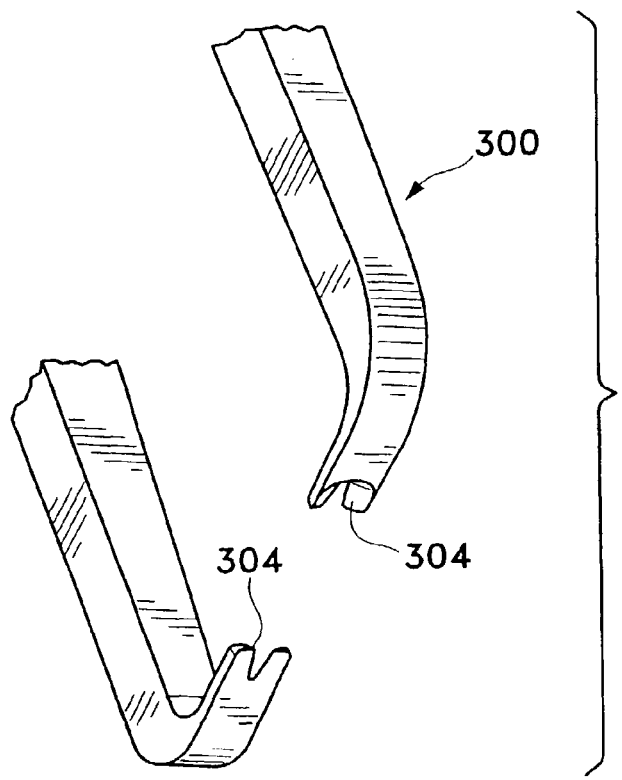
FIG. 22 shows another variation on the apparatus of FIGS. 19A-C.

Other tip configurations also can be used with this tweezers-style removal tool such as the variations shown in FIGS. 21 and 22. Most notably, one leg of the tweezers can have a double edge head at the end of it (FIG. 21). In other words, there are two protruding members, side-by-side at the tip. These two protruding members have enough space between them to allow the opposing protruding member on the other leg to slide between them. This configuration provides a more desirable bend in the clip, thus allowing easier removal. In FIG. 22, the beveled ends are turned about 90 degrees as compared to those in FIG. 19A.

Apparatus 200, with the "Hook and Slide" design, lends itself to standard conventional manufacturing techniques. The hook itself can be made from drawn wire (stainless steel or Nitinol) which has been machined at the tip to form the hook. Wire EDM or laser cutting could also be used to form this hook at the end of the wire. The handle and finger slider (or squeeze buttons) are best injection molded from any number of plastic resins, most likely ABS. The handle halves could then be easily sonic welded together. It is conceivable that these parts could be machined from metal or some other material, although this would be a much costlier option. The outer tube which slides over the hook can be extruded or drawn metal or plastic.

The "Shearing Tweezers" design has only two parts, both of which are machined form stainless steel or titanium blanks. The two machined pieces are welded together up near the top of the handle area.

In use, the instrument apparatus 200 is held by the surgeon in similar fashion to a pencil or surgical instrument, such as forceps or a probe. The hook is guided down to the clip and hooked around any part of the clip, preferably at a right angle to the clip. Once the hook is secured on the clip, the hook (with clip) is retracted into the outer tube of the device using the finger slider or squeeze buttons. If it is the wire loop or lasso, the loop must go over one of the free ends of the clip. The loop is then slid up onto the main part of the clip and then retracted (with the clip) into the outer tube using the finger slider or squeeze buttons. At this point the clip is out of the tissue and completely contained within the outer tube. It can be retrieved by reversing the action of the finger slider or squeeze buttons to push it out of the tube.

The "Shearing Tweezers" are also simple to operate. The shearing tweezers are held just as any other surgical tweezers or forceps would be held. The surgeon guides the distal tip with the protruding member down to the clip and again, preferably at a right angle, slides the protruding member onto the clip. This is done so that the clip is resting in the bottom of the "V" groove, with one tine of the fork under the clip (between clip and tissue) and the other tine over the clip. Once in this position, the legs of the tweezers are squeezed closed. It sometimes requires multiple squeezes to be able to fully extract the clip. The tweezers design is well suited for reuse and sterilization, as it is made of only two parts, which are welded together to form one. A more comprehensive description of removal tools and procedures can be had by referring to our copending, commonly assigned application (Ser. No. not yet assigned) filed on even date herewith, titled "Surgical Clip Removal Apparatus", which is hereby incorporated herein in its entirety, by reference thereto.

All references cited herein are incorporated by reference in their entirety.

While the above is a complete description of the preferred embodiments of the present invention, various alternatives, modifications and equivalents may be used. Therefore, the above description should not be taken as limiting the scope of the invention, which is defined by the following claims.

The invention claimed is:

1. A surgical fastener comprising a shaped clip element self-transitionable from an open configuration to a closed configuration, and a shaped double coil exteriorly coiled about and surrounding at least a portion of said clip element and movable between said open configuration and said closed configuration, each of said clip element and said coil being shaped to assume said closed configuration when in a free state, wherein said clip element possesses a memory set shape of said closed configuration apart from said coil.

2. The surgical fastener of claim 1, wherein said double coil comprises Nitinol.

3. The surgical fastener of claim 1, wherein said closed configuration includes said clip element forming a single loop.

4. The surgical fastener of claim 1, wherein said shaped double coil includes first and second wires exteriorly coiled side-by-side about said at least a portion of said clip.

5. The surgical fastener of claim 4, wherein a diameter of said first wire is the same as a diameter of said second wire.

6. The surgical fastener of claim 4, wherein an outer diameter of coil windings of said first wire is the same as an outer diameter of coil windings of said second wire.

7. The surgical fastener of claim 4, wherein each of said first and second wires comprises Nitinol.

8. A surgical fastener comprising a shaped clip element movable between an open configuration and a closed configuration, and a shaped coil comprising more than two wires, said shaped coil surrounding at least a portion of said clip element such that said shaped coil is exteriorly exposed relative to said portion and self-transitionable from said open configuration to said closed configuration, each of said clip element and said coil being shaped to assume said closed configuration when in a free state, wherein said clip element possesses a memory set shape of said closed configuration apart from said coil.

9. The surgical fastener of claim 8, wherein said coil comprises Nitinol.

10. A surgical fastener comprising:
a shaped clip element self-transitionable from an open configuration to a closed configuration;
a shaped coil surrounding at least a portion of said clip element and movable between said open configuration and said closed configuration, each of said clip element and said coil being shaped to assume said closed configuration when in a free state;
wherein said clip element possesses a memory set shape of said closed configuration apart from said coil
two restraints on said clip element, said coil extending between said two restraints in said closed configuration; and
a release mechanism adapted to engage said clip element at least one of said restraints and to apply a bias force onto said coil, said coil configured to force said clip element into said open configuration in response to said bias force.

11. The surgical fastener of claim 10, wherein said coil is integrally mounted to said clip element and is adapted to remain integral with said clip element in said closed configuration.

12. The surgical fastener of claim 10, wherein said clip element comprises a wire having a shape memory which defines said closed configuration, said closed configuration being substantially spiral-shaped.

13. The surgical fastener of claim 12, wherein said wire comprises Nitinol.

14. The surgical fastener of claim 10, wherein said coil has a shape memory which substantially conforms to said closed configuration.

15. The surgical fastener of claim 14, wherein said closed configuration is substantially spiral-shaped.

16. The surgical fastener of claim 14, wherein said coil comprises Nitinol.

17. The surgical fastener of claim 10, wherein said release mechanism is configured to apply said bias force by forcing one of said restraints toward an other of said restraints.

* * * * *